(12) United States Patent
Tian

(10) Patent No.: US 10,126,202 B2
(45) Date of Patent: Nov. 13, 2018

(54) METHOD FOR AUTOMATICALLY ESTIMATING INERTIA, COULOMB FRICTION, AND VISCOUS FRICTION IN A MECHANICAL SYSTEM

(71) Applicant: LINESTREAM TECHNOLOGIES, Cleveland, OH (US)

(72) Inventor: Gang Tian, Westlake, OH (US)

(73) Assignee: LINESTREAM TECHNOLOGIES, Cleveland, OH (US)

(*) Notice: Subject to any disclaimer, the term of this patent is extended or adjusted under 35 U.S.C. 154(b) by 469 days.

(21) Appl. No.: 14/851,307

(22) Filed: Sep. 11, 2015

(65) Prior Publication Data

US 2017/0074753 A1 Mar. 16, 2017

(51) Int. Cl.
| | | |
|---|---|---|
| *G06F 11/30* | (2006.01) | |
| *G01M 13/02* | (2006.01) | |
| *G01M 1/10* | (2006.01) | |
| *G21C 17/00* | (2006.01) | |
| *G01N 19/02* | (2006.01) | |

(52) U.S. Cl.
CPC ............ *G01M 13/025* (2013.01); *G01M 1/10* (2013.01); *G01N 19/02* (2013.01)

(58) Field of Classification Search
CPC .................................................. G01M 13/025
See application file for complete search history.

(56) References Cited

U.S. PATENT DOCUMENTS

| | | |
|---|---|---|
| 3,543,010 A | 11/1970 | Dahlin |
| 3,786,242 A | 1/1974 | Brooks |
| 3,826,887 A | 7/1974 | Pemberton |
| 4,481,567 A | 11/1984 | Kaya et al. |
| 4,540,923 A | 9/1985 | Kade et al. |

(Continued)

FOREIGN PATENT DOCUMENTS

| | | |
|---|---|---|
| EP | 0827265 | 4/2002 |
| JP | 2002-023807 | 1/2002 |

(Continued)

OTHER PUBLICATIONS

Aaron, "Synthesis of Feedback Control Systems by Means of Pole and Zero Location of the Closed Loop Function". AIEE Transactions, 1951, vol. 70, 8 pages.

(Continued)

*Primary Examiner* — Phuong Huynh
(74) *Attorney, Agent, or Firm* — Amin, Turocy & Watson LLP

(57) ABSTRACT

Systems and methods for estimating an inertia, a Coulomb friction coefficient, and a viscous friction coefficient for a controlled mechanical system are provided. In one or more embodiments, an inertia and friction estimation system can generate a torque command signal that varies continuously over time during a testing sequence. The velocity of a motion system in response to the time-varying torque command signal is measured and recorded during the testing sequence. The estimation system then estimates the inertia and the friction coefficients of the motion system based on the torque command data sent to the motion system and the measured velocity data. In some embodiments, the estimation system estimates the inertia and the friction coefficients based on integrals of the torque command data and the velocity data.

20 Claims, 14 Drawing Sheets

(56) References Cited

U.S. PATENT DOCUMENTS

| | | |
|---|---|---|
| 4,768,143 A | 8/1988 | Lane et al. |
| 5,159,254 A | 10/1992 | Teshima |
| 5,229,699 A | 7/1993 | Chu et al. |
| 5,602,347 A | 2/1997 | Matsubara et al. |
| 5,684,375 A | 11/1997 | Chaffee et al. |
| 5,742,503 A | 4/1998 | Yu |
| 6,037,736 A | 3/2000 | Tsuruta et al. |
| 6,122,555 A | 9/2000 | Lu |
| 6,128,541 A | 10/2000 | Junk |
| 6,198,246 B1 | 3/2001 | Yutkowitz |
| 6,445,962 B1 | 9/2002 | Blevins et al. |
| 6,495,791 B2 | 9/2002 | Sawatsky et al. |
| 6,510,353 B1 | 1/2003 | Gudaz et al. |
| 6,546,295 B1 | 4/2003 | Pyotsia et al. |
| 6,564,194 B1 | 5/2003 | Koza et al. |
| 6,611,125 B2 | 8/2003 | Nagata et al. |
| 6,631,299 B1 | 10/2003 | Patel et al. |
| 6,658,305 B1 | 12/2003 | Gudmundsson et al. |
| 6,980,869 B1 | 12/2005 | Chandhoke |
| 7,024,253 B2 | 4/2006 | Gaikwad et al. |
| 7,149,591 B2 | 12/2006 | Gao et al. |
| 7,289,915 B2 | 10/2007 | Ide |
| 7,346,402 B1 | 3/2008 | Stahl |
| 7,449,857 B2 | 11/2008 | Oha et al. |
| 7,865,254 B2 | 1/2011 | Gahinet et al. |
| 8,041,436 B2 | 10/2011 | Gao |
| 8,060,340 B2 | 11/2011 | Gao et al. |
| 8,146,402 B2 | 4/2012 | Collins et al. |
| 2003/0139825 A1 | 7/2003 | Lund |
| 2005/0034538 A1 | 2/2005 | Rehm et al. |
| 2007/0073422 A1 | 3/2007 | Gaikwad et al. |
| 2007/0088448 A1 | 4/2007 | Mylaraswamy et al. |
| 2008/0203960 A1 | 8/2008 | Golownia et al. |
| 2008/0291272 A1 | 11/2008 | Krahnstoever et al. |
| 2013/0278196 A1 | 10/2013 | Tian |
| 2014/0109647 A1 | 4/2014 | Faivre et al. |
| 2014/0139170 A1 | 5/2014 | Tian |
| 2014/0365143 A1 | 12/2014 | Henley et al. |

FOREIGN PATENT DOCUMENTS

| | | | |
|---|---|---|---|
| JP | 2006-333570 | | 12/2006 |
| KR | 10-1121474 | | 1/2012 |
| WO | 0041043 A1 | | 7/2000 |
| WO | 2013/158849 | | 10/2013 |
| WO | WO 2013158849 A2 * | 10/2013 | ............. H02P 23/14 |
| WO | 2014-089119 | | 6/2014 |

OTHER PUBLICATIONS

Gao, et al., "A Novel Motion Control Design Approach Based on Active Disturbance Rejection". Proceedings of the 40th IEEE Conference on Decision and Control, Orlando, Florida USA, Dec. 2001, 0-7803-7061-9/01 (c)2001 IEEE, 6 pages.

Ghanekar, et al., "Scaling Laws for Frequency Domain Controllers of Dynamically Equivalent Single Flexible Link Manipulators". IEEE International Conference on Robotics and Automation, 0-7803-1965-6/95 (c)1995 IEEE, 6 pages.

Ghanekar, et al., "Scaling Laws for Linear Controllers of Flexible Link Manipulators Characterized by Nondimensional Groups". IEEE Transactions on Robotics and Automation, vol. 13, No. 1, Feb. 1997, 1042-296X/97 (c)1997 IEEE, 11 pages.

Suh, et al., "New PID Identification Algorithm Based on Frequency Scaling", 0-7803-3694-1/97 (c)1997 IEEE, 5 pages.

International Search Report & Written Opinion for PCT Application Serial No. PCT/US2016/050636, dated Nov. 23, 2016, 21 pages.

* cited by examiner

METHOD FOR AUTOMATICALLY ESTIMATING INERTIA, COULOMB FRICTION, AND VISCOUS FRICTION IN A MECHANICAL SYSTEM

TECHNICAL FIELD

This disclosure generally relates to motion control, and more specifically, to estimation of inertias and friction coefficients for use as parameters in a motion control system.

BACKGROUND

Many automation applications employ motion control systems to control machine position and speed. Such motion control systems typically include one or more motors or similar actuating devices operating under the guidance of a controller, which sends position and speed control instructions to the motor in accordance with a user-defined control algorithm. Some motion control systems operate in a closed-loop configuration, whereby the controller instructs the motor to move to a target position or to transition to a target velocity (a desired state) and receives feedback information indicating an actual state of the motor. The controller monitors the feedback information to determine whether the motor has reached the target position or velocity, and adjusts the control signal to correct errors between the actual state and the desired state.

Designers of motion control systems seek to achieve an optimal trade-off between motion speed and system stability. For example, if the controller commands the motor to transition a mechanical component to a target position at a high torque, the machine may initially close the distance between the current position and the desired position at high speed (and thus in a time-efficient manner), but is likely to overshoot the desired position because of the high torque. Consequently, the controller must apply a corrective signal to bring the machine back to the desired position. It may take several such iterations before the motion system converges on the desired position, resulting in undesired machine oscillations. Conversely, instructing the motor to move at a lower torque may increase the accuracy of the initial state transition and reduce or eliminate machine oscillation, but will increase the amount of time required to place the machine in the desired position. Ideally, the controller gain coefficients should be selected to optimize the trade-off between speed of the state transition and system stability. The process of selecting suitable gain coefficients for the controller is known as tuning.

The response of a controlled mechanical system to a signal from a controller having a given set of controller gain coefficients depends on physical characteristics of the mechanical system, including the inertia and friction. Inertia represents the resistance of the motion system to acceleration or deceleration. Friction is a resistive force resulting from the sliding contact between physical components of the system, such as the contact between the rotor and the shaft. The system's total friction can be modeled as a combination of its Coulomb friction and viscous friction. FIG. 1 is a simplified model 100 of a system's combined Coulomb and viscous friction as a function of is speed. The system's Coulomb friction has a relatively constant magnitude represented by the magnitude of the friction just as the system begins moving from a state of rest. Coulomb friction can be represented by point 102a when the system is moving in the forward direction, and point 102b when moving in the reverse direction. The viscous friction, which represents a frictional force which may be a function of lubrication between moving parts of the system, has a magnitude that typically increases with the magnitude of the speed, and is represented by the slopes 104a and 104b in the simplified model 100.

Accurate estimates for the inertia and friction of a controlled mechanical system can simplify the tuning process and improve performance of the system. However, identifying accurate values for these parameters for a given mechanical system can be difficult. In some cases, the inertia is estimated using manual calculations based on the rated motor data and physical data (weight, dimensions, etc.) of the components comprising the load. Such calculations can be cumbersome and time consuming, and may not yield accurate values for these important parameters.

The above-described is merely intended to provide an overview of some of the challenges facing conventional motion control systems. Other challenges with conventional systems and contrasting benefits of the various non-limiting embodiments described herein may become further apparent upon review of the following description.

SUMMARY

The following presents a simplified summary of one or more embodiments in order to provide a basic understanding of such embodiments. This summary is not an extensive overview of all contemplated embodiments, and is intended to neither identify key or critical elements of all embodiments nor delineate the scope of any or all embodiments. Its purpose is to present some concepts of one or more embodiments in a simplified form as a prelude to the more detailed description that is presented later.

One or more embodiments of the present disclosure relate to systems and methods for automatically estimating the inertia, viscous friction coefficient, and Coulomb friction coefficient for controlled mechanical systems. To this end, an inertia and friction estimation system can instruct a controller to send a torque control signal to a motor, where the torque control signal varies continuously over time. This torque control signal can be controlled based on a testing sequence defined in the inertia and friction estimation system. In one or more embodiments, the testing sequence can specify that the torque control signal will increase gradually at a defined rate of increase, causing the motor to accelerate. In response to the velocity of the motion system satisfying a defined criterion, the torque control signal will then gradually decrease, causing the motor to decelerate to a rest state.

During these acceleration and deceleration phases, the inertia estimation system measures and records the velocity of the motor over time in response to the torque control signal. The estimation system can then determine an estimated inertia, an estimated viscous friction coefficient, and an estimated Coulomb friction coefficient for the mechanical system based on the time-varying torque signal and the measured velocity curve. These estimated inertia and friction coefficients can be used by the system designer in connection with determining suitable control parameters for the motion system. For example, the estimated inertia and/or the friction coefficients can be used by the controller to facilitate identification of appropriate controller gains for the system.

The following description and the annexed drawings set forth herein detail certain illustrative aspects of the one or more embodiments. These aspects are indicative, however, of but a few of the various ways in which the principles of

DETAILED DESCRIPTION

Figure 1:
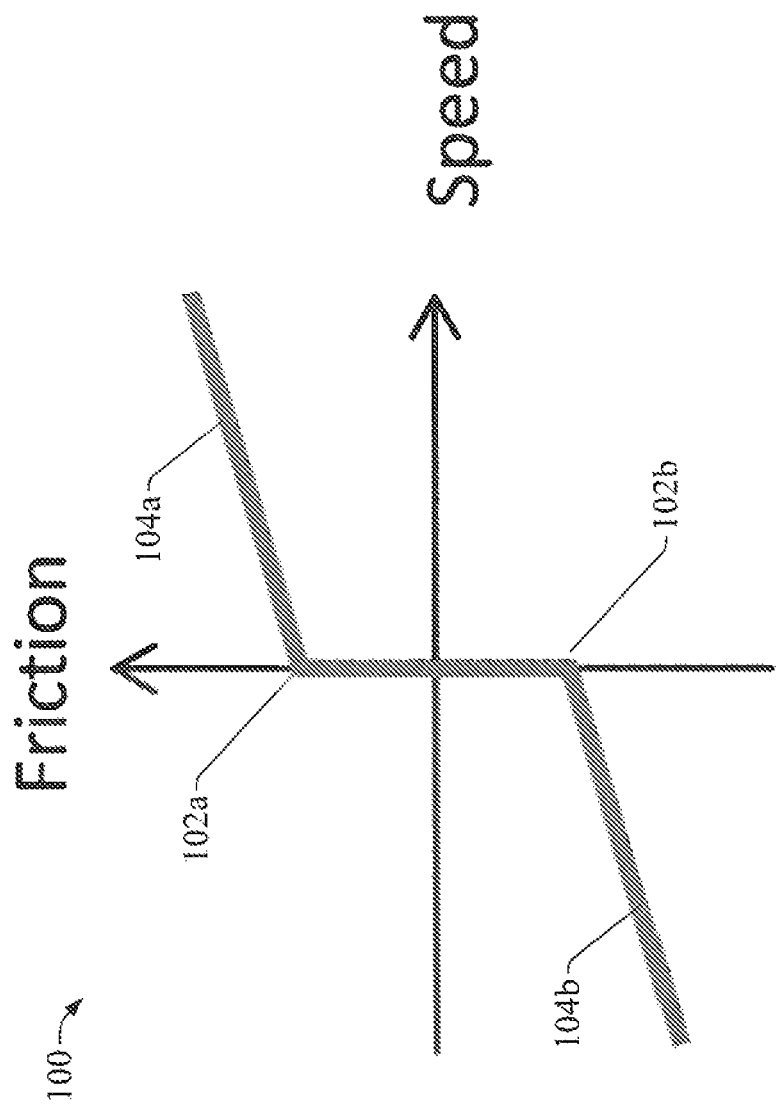
FIG. 1 is a simplified model of a system's combined Coulomb and viscous friction as a function of is speed.

Various embodiments are now described with reference to the drawings, wherein like reference numerals refer to like elements throughout. In the following description, for the purposes of explanation, numerous specific details are set forth in order to provide an understanding of this disclosure. It is to be understood, however, that such embodiments may be practiced without these specific details, or with other methods, components, materials, etc. In other instances, structures and devices are shown in block diagram form to facilitate describing one or more embodiments.

Systems and methods described herein relate to techniques for generating estimated inertia, viscous friction coefficient, and Coulomb friction coefficient for controlled mechanical systems. One or more embodiments of the present disclosure can estimate these parameters in a substantially automated fashion by running the mechanical system through a testing sequence to be defined in more detail herein. Results of this testing sequence can be used to generate accurate inertia, viscous friction coefficient, and Coulomb friction coefficient estimates for the system. These estimated parameters can subsequently be used to facilitate simplified and accurate tuning and control of the motion system.

Figure 2:
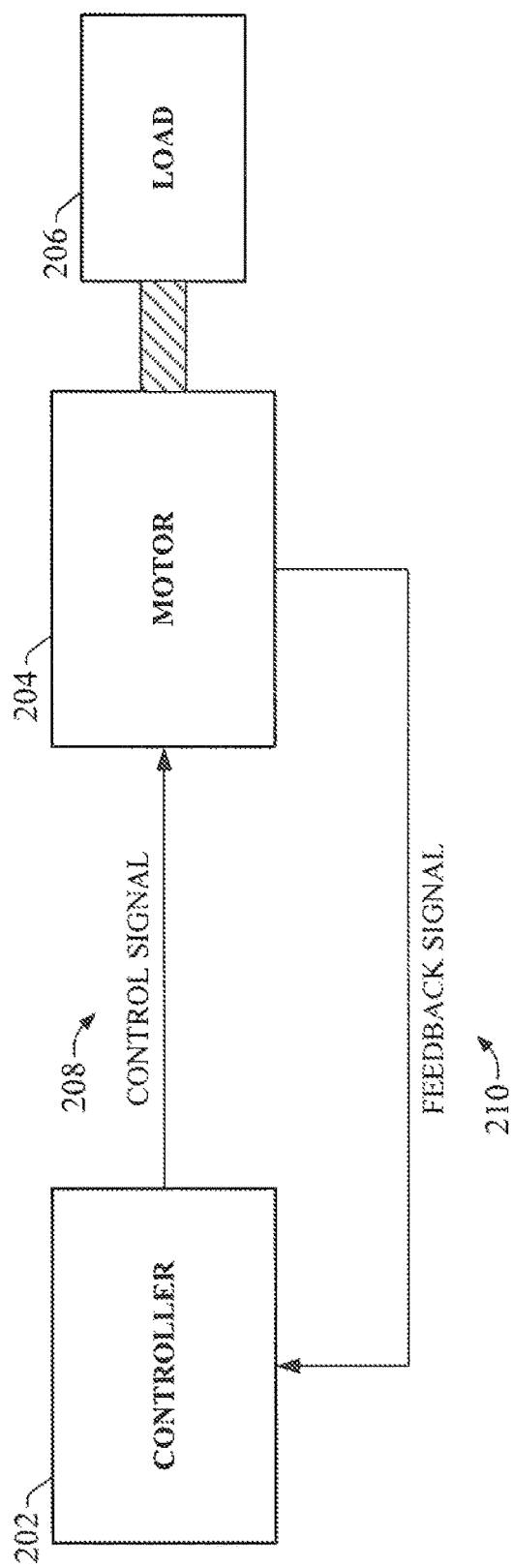
FIG. 2 is a simplified diagram of a closed-loop motion control architecture.

FIG. 2 is a simplified diagram of a closed-loop motion control architecture. Controller 202 is programmed to control motor 204, which drives mechanical load 206. Controller 202, motor 204, and load 206 comprise the primary components of an exemplary motion control system. In an example application, load 206 can represent an axis of a single- or multi-axis robot or positioning system. In such applications, controller 202 sends control signal 208 instructing the motor 204 to move the load 106 to a desired position at a desired speed. The control signal 208 can be provided directly to the motor 204, or to a motor drive (not shown) that controls the power delivered to the motor 204 (and consequently the speed and direction of the motor). Feedback signal 210 indicates a current state (e.g., position, velocity, etc.) of the motor 204 and/or load 206 in substantially real-time. In servo-driven systems, feedback signal 210 can be generated, for example, by an encoder or resolver (not shown) that tracks an absolute or relative position of the motor. In sensorless systems lacking a velocity sensor, the feedback signal can be provided by a speed/position estimator. During a move operation, the controller monitors feedback signal 210 to ensure that the load 206 has accurately reached the target position. The controller 202 compares the actual position of the load as indicated by the feedback signal 210 with the target position, and adjusts the control signal 208 as needed to reduce or eliminate error between the actual and target positions.

In another example application, load 206 can represent a spinning load (e.g., a pump, a washing machine, a centrifuge, etc.) driven by motor 204, in which controller 202 controls the rotational velocity of the load. In this example, controller 202 provides an instruction to motor 204 (via control signal 208) to transition from a first velocity to a second velocity, and makes necessary adjustments to the control signal 208 based on feedback signal 210. It is to be appreciated that the parameter estimation techniques of the present application are not limited to use with the example types of motion control systems described above, but rather are applicable for substantially any type of motion control application.

The control signal output generated by the controller 202 in response to an error between the desired position or velocity and the target position or velocity (as reported by the feedback signal 210) depends on the gain coefficients for the control loop. Design engineers must often employ a trial-and-error approach to identifying suitable gain coefficients (i.e. tuning the control loop), since suitable gain selection depends on physical characteristics of the mechanical system being controlled. For example, mechanical systems with a high inertia (resistance to acceleration or deceleration) may require relatively high initial torque to initiate a move to a new position or velocity, particularly if the application requires rapid convergence on the target position/velocity. However, high torque commands increase the possibility of overshoot, necessitating a reverse correction to bring the system back to the target. Non-optimal gain settings can result in undesired mechanical oscillations as the system performs multiple corrective iterations before settling on the target position or velocity. Such oscillations can introduce instability, cause system delays, and consume excessive power as a result of the additional work required to bring the system to a stable state. The friction of the motor and other moving parts can also affect how the mechanical system responds to a given control signal, and is therefore a factor to be considered when tuning the control system.

Control system tuning can be simplified if accurate estimates of the mechanical system's inertia and friction coefficients are known. Knowledge of these parameters can also improve performance of the controlled system during operation. For example, accurate estimates of a mechanical system's Coulomb and viscous friction coefficients can assist an engineer in designing the control system to more effectively compensate for these factors. However, identifying accurate inertia and friction coefficients for a mechanical system can be difficult. Accordingly, one or more embodiments of the present disclosure provide a technique for accurately estimating a controlled mechanical system's inertia, viscous friction coefficient, and Coulomb friction coefficient in a substantially automated fashion.

Figure 3:
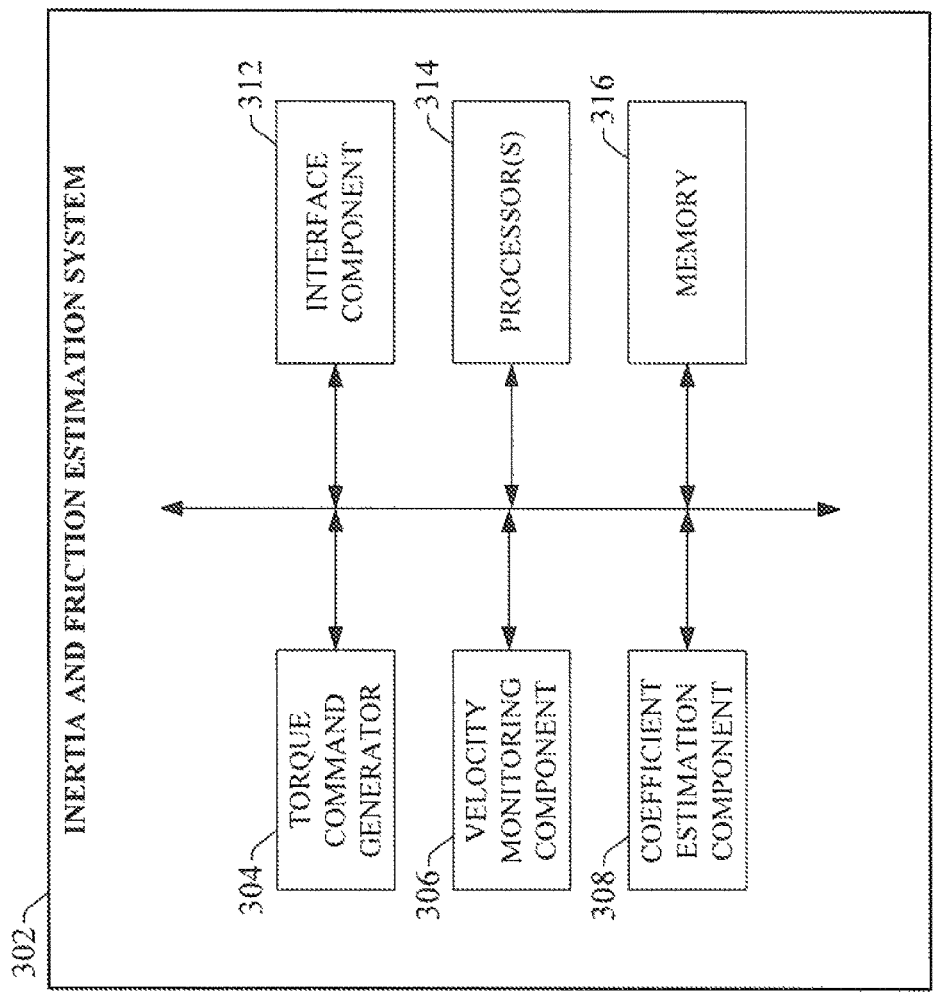
FIG. 3 is a block diagram of an example inertia and friction estimation system capable of generating estimated values of a mechanical system's inertia, viscous friction coefficient, and Coulomb friction coefficient.

FIG. 3 is a block diagram of an example inertia and friction estimation system capable of generating estimated values of a mechanical system's inertia, viscous friction coefficient, and Coulomb friction coefficient. Inertia and friction estimation system 302 can include a torque command generator 304, a velocity monitoring component 306, a coefficient estimation component 308, an interface component 312, one or more processors 314, and memory 316. In various embodiments, one or more of the torque command generator 304, velocity monitoring component 306, coefficient estimation component 308, interface component 312, the one or more processors 314, and memory 318 can be electrically and/or communicatively coupled to one another to perform one or more of the functions of the inertia and friction estimation system 302. In some embodiments, components 304, 306, 308, and 312 can comprise software instructions stored on memory 316 and executed by processor(s) 314. The inertia and friction estimation system 302 may also interact with other hardware and/or software components not depicted in FIG. 3. For example, processor(s) 314 may interact with one or more external user interface device, such as a keyboard, a mouse, a display monitor, a touchscreen, or other such interface devices.

Interface component 312 can be configured to receive user input and to render output to the user in any suitable format (e.g., visual, audio, tactile, etc.). User input can be, for example, user-entered parameters used by the inertia and friction estimation system 302 when executing an estimation sequence (to be described in more detail below). Torque command generator 304 can be configured to output a torque control command that various continuously over time according to a defined testing sequence. Velocity monitoring component 306 can receive velocity data for the mechanical system for use in calculating the inertia and friction coefficients. In some embodiments, the velocity monitoring component 306 can measure and record the velocity of the motor over time in response to the applied torque control command generated by the torque command generator 304. Alternatively, the velocity monitoring component 306 can receive the measured velocity data from separate measuring instrumentation.

Coefficient estimation component 308 can be configured to generate estimates of the inertia, viscous friction coefficient, and Coulomb friction coefficient of a motion system. The coefficient estimation component 308 determines these estimated parameters based on the time-varying torque command generated by torque command generator 304 and the measured velocity curve acquired by the velocity monitoring component 306, according to a model to be described in more detail below. The one or more processors 314 can perform one or more of the functions described herein with reference to the systems and/or methods disclosed. Memory 316 can be a computer-readable storage medium storing computer-executable instructions and/or information for performing the functions described herein with reference to the systems and/or methods disclosed.

Figure 4:
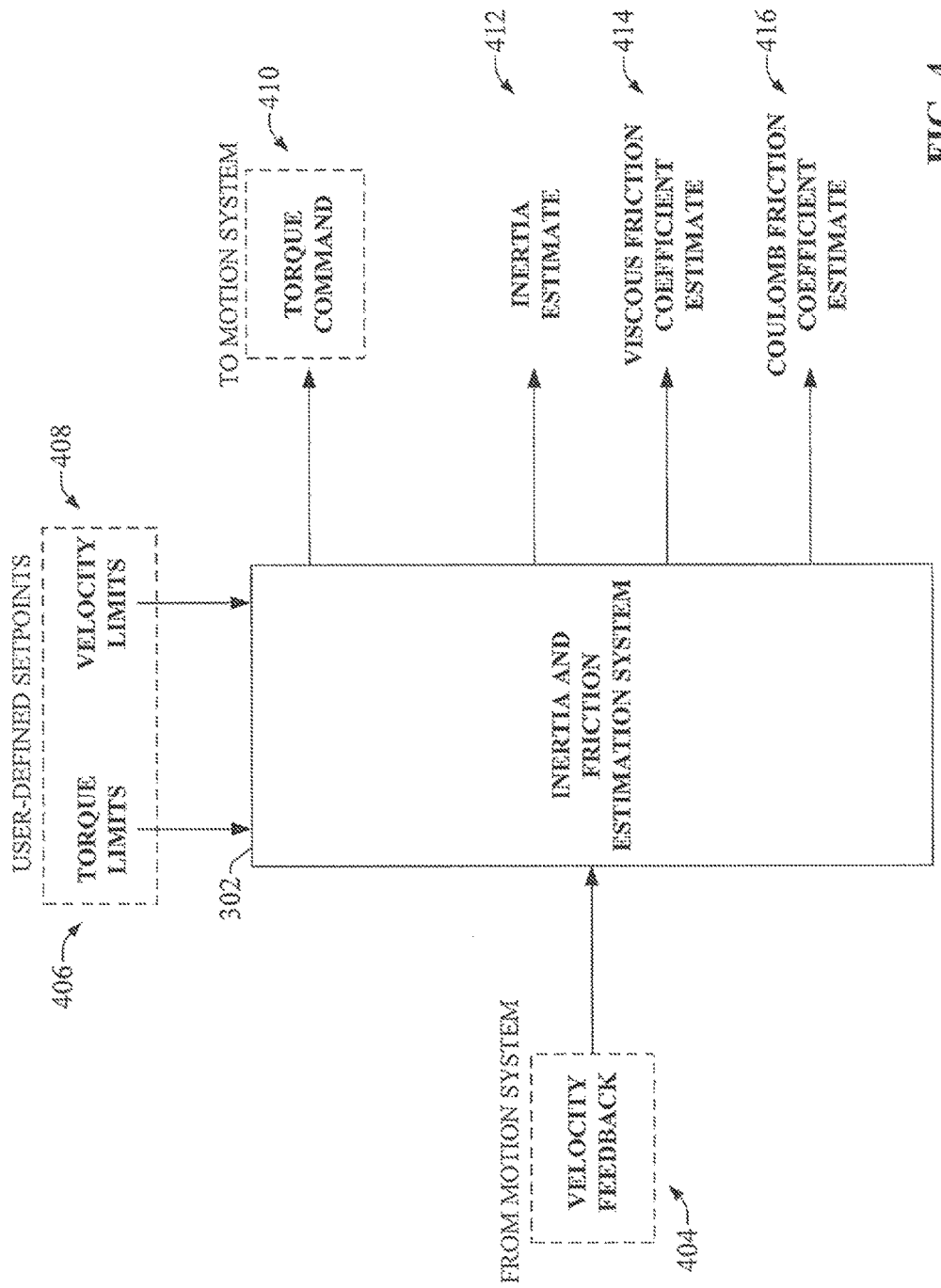
FIG. 4 is a block diagram illustrating the inputs and outputs associated with an inertia and friction estimation system.

The inertia and friction estimation system 302 can generate estimates for a mechanical system's inertia and friction coefficients by running the system through a testing sequence and calculating the estimates based on the results. FIG. 4 is a block diagram illustrating the inputs and outputs associated with inertia and friction estimation system 302. Inertia and friction estimation system 302 can generate a torque command signal 410 (e.g., an analog voltage signal such as a 0-10 VDC signal, an analog current signal such as a 4-20 mA signal, a digital signal, a software instruction, or any other suitable type of control signal), which instructs a motor driving the motion system to rotate in a specified direction at a given torque. Rather than issuing one or more constant torque commands that transition between constant torque values in sudden steps (resulting in a step-shaped torque output), inertia and friction estimation system 302 can control torque command signal 410 such that the torque value varies continuously over time between a maximum and minimum torque value. Inertia and friction estimation system 302 controls the torque value issued via torque command signal 410 in accordance with a testing sequence having user-defined parameters, as will be discussed in more detail below.

The motion system will accelerate or decelerate in accordance with the torque command signal 410 issued by inertia and friction estimation system 302, and velocity feedback 404 from the motion control system is provided to the estimation system 302. Velocity feedback 404 represents the velocity of the motion system over time in response to application of torque command signal 410. In an example testing sequence, inertia and friction estimation system 302 can control torque command signal 410 as a function of the velocity feedback 404 and one or more user-defined setpoints. The user-defined setpoints can include torque limits 406 defining the upper and lower bounds of the torque command signal 410, and velocity limits 408 defining checkpoint velocity valves used to control the torque command signal 410 and generate the estimates.

Upon completion of the testing sequence, inertia and friction estimation system 302 generates estimates of the motion system's inertia 412, viscous friction coefficient 414, and Coulomb friction coefficient 416. Inertia and friction estimation system 302 determines these estimates based on the torque command signal 410 that was issued to the motion system and the corresponding velocity feedback 404. In one or more embodiments, inertia and friction estimation system 302 can integrate selected portions of the torque curve (corresponding to torque command signal 410) and the velocity curve (corresponding to velocity feedback 404) over time, and calculate the inertia estimate 412, viscous friction estimate 414, and Coulomb friction estimate 416 as functions of these integrals.

Figure 5:
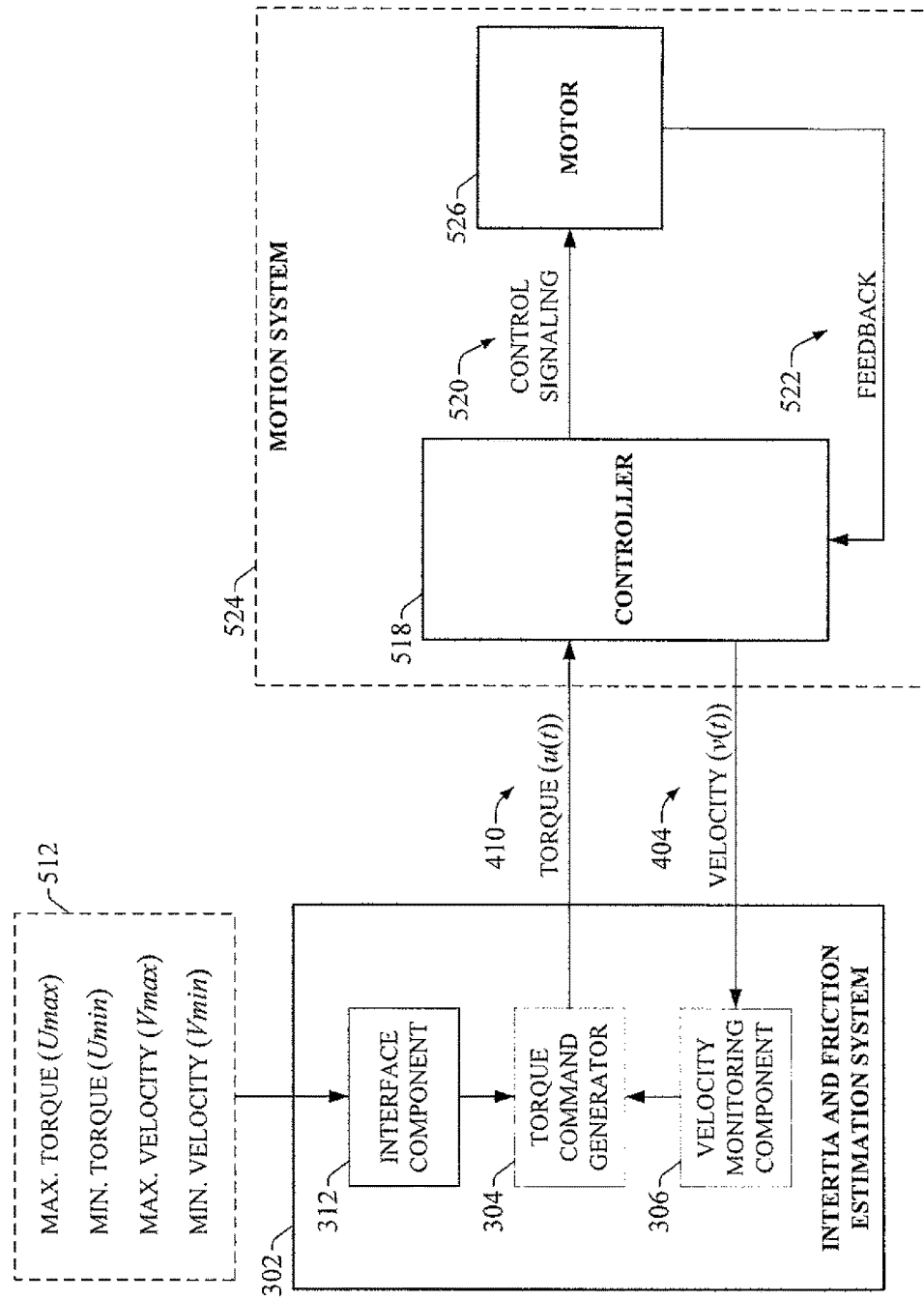
FIG. 5 is a diagram illustrating interactions between an inertia and friction estimation system and a motion control system during an example testing sequence.

FIG. 5 is a diagram illustrating interactions between inertia and friction estimation system 302 and a motion control system during an example testing sequence. In this example, motion system 524 comprises a motor 526, which responds to control signaling 520 provided by controller 518. Motor 526 is used to drive a load (not shown), such as a positioning axis, a rotational component of a machine, or other motor-driven load. Controller 518 also monitors feedback 522, which provides substantially real-time state data for the motor 526 (e.g., position, speed, etc.). In some scenarios, controller 518 may be a hardware controller, such as a programmable logic controller, motor drive, or other type of hardware controller. Controller 518 may also be a system-on-chip or other type of silicon-based or microchip controller in some implementations.

In the illustrated example, inertia and friction estimation system 302 is depicted as a separate element from controller 518 for clarity. For such configurations, and friction estimation system 302 can exchange data with controller 518 or other elements of the motion system 524 via any suitable communications means, including but not limited to wired or wireless networking, hardwired data links, or other communication means. In other embodiments, inertia and friction estimation system 302 can be an integrated component of controller 518. For example, inertia and friction estimation system 302 can be a functional component of the controller's operating system and/or control software executed by one or more processors residing on the controller 518. Inertia and friction estimation system 302 can also be a hardware component residing within controller 518, such as a circuit board or integrated circuit, that exchanges data with other functional elements of the controller 518. Other suitable implementations of inertia and friction estimation system 302 are within the scope of certain embodiments of the present disclosure.

Prior to testing, one or more user-defined parameters 512 are provided to inertia and friction estimation system 302 via interface component 312. These parameters can include a maximum torque Umax and a minimum torque Umin defining upper and lower limits on the torque command signal to be generated by torque command generator 304. In some embodiments, the estimation system 302 may only require the maximum torque Umax to be defined by the user, and can use the magnitude of the defined maximum torque as a limiting value for both the forward and reverse directions. In other embodiments, estimation system 302 may accept values for both Umax and Umin, allowing for different torque setpoints for the forward and reverse directions, respectively. The values selected for Umax and Umin can correspond to the expected operational limits of the motion system 524, thereby allowing the inertia and friction coefficients to be determined based on characteristics of the motion system 524 over the system's entire torque profile. User-defined parameters 512 can also include a maximum velocity Vmax and a minimum velocity Vmin, which represent critical velocities used to define stages of the test sequence, as will be described in more detail below. It is to be understood that the defined maximum and minimum velocities do not necessarily correspond to the maximum and minimum operating velocities of the motor, or the maximum and minimum velocities that the motor will achieve during the testing sequence, but rather define key checkpoint velocities that, when reached during the testing sequence, will trigger a new phase of the testing sequence.

Interface component 312 provides torque command generator 304 with the user-defined parameters 512. When testing is initiated, torque command generator 304 outputs a torque command signal 410 to the motion system 524. Torque command signal 410 is represented as u(t), since the torque command generator 304 will vary the torque command continuously over time. In the configuration depicted in FIG. 5, estimation system 302 sends torque command signal 410 to controller 518, which in turn instructs the motor 526 (via control signaling 520) to rotate in the indicated direction at the indicated torque. As the motor is rotating, velocity monitoring component 306 reads velocity feedback 404 from controller 518 (which itself measures the velocity of the motor 526 via feedback 522). The measured velocity feedback 404 over time is represented as v(t). As testing proceeds, torque command generator 304 can vary the torque command signal 410 in accordance with a pre-defined testing sequence, wherein phases of the testing sequence are triggered by the velocity feedback 404 relative to the user-defined parameters 512.

An example testing sequence is now explained with reference to FIG. 6, which illustrates an example torque command signal u(t) and corresponding velocity feedback v(t) graphed over time. As shown on torque graph 602, the torque command signal u(t) is bounded by Umax and Umin. Velocity parameters Vmax and Vmin, shown on velocity graph 604, will determine phase transitions of the testing sequence. The values of Umax, Umin, Vmax, and Vmin can be defined by the user prior to testing (e.g., as user-defined parameters 512 of FIG. 5). In general, the estimation system 302 will apply a continuous torque signal that accelerates and then decelerates the motion system according to a defined sequence, obtain the continuously measured velocity of the motion system in response to the applied toque signal, and calculate the inertia ratio, Coulomb friction coefficient, and viscous friction coefficient of the motion system based on the torque signal, the velocity feedback data, and a calculation model that will be described in more detail below.

Figure 6:
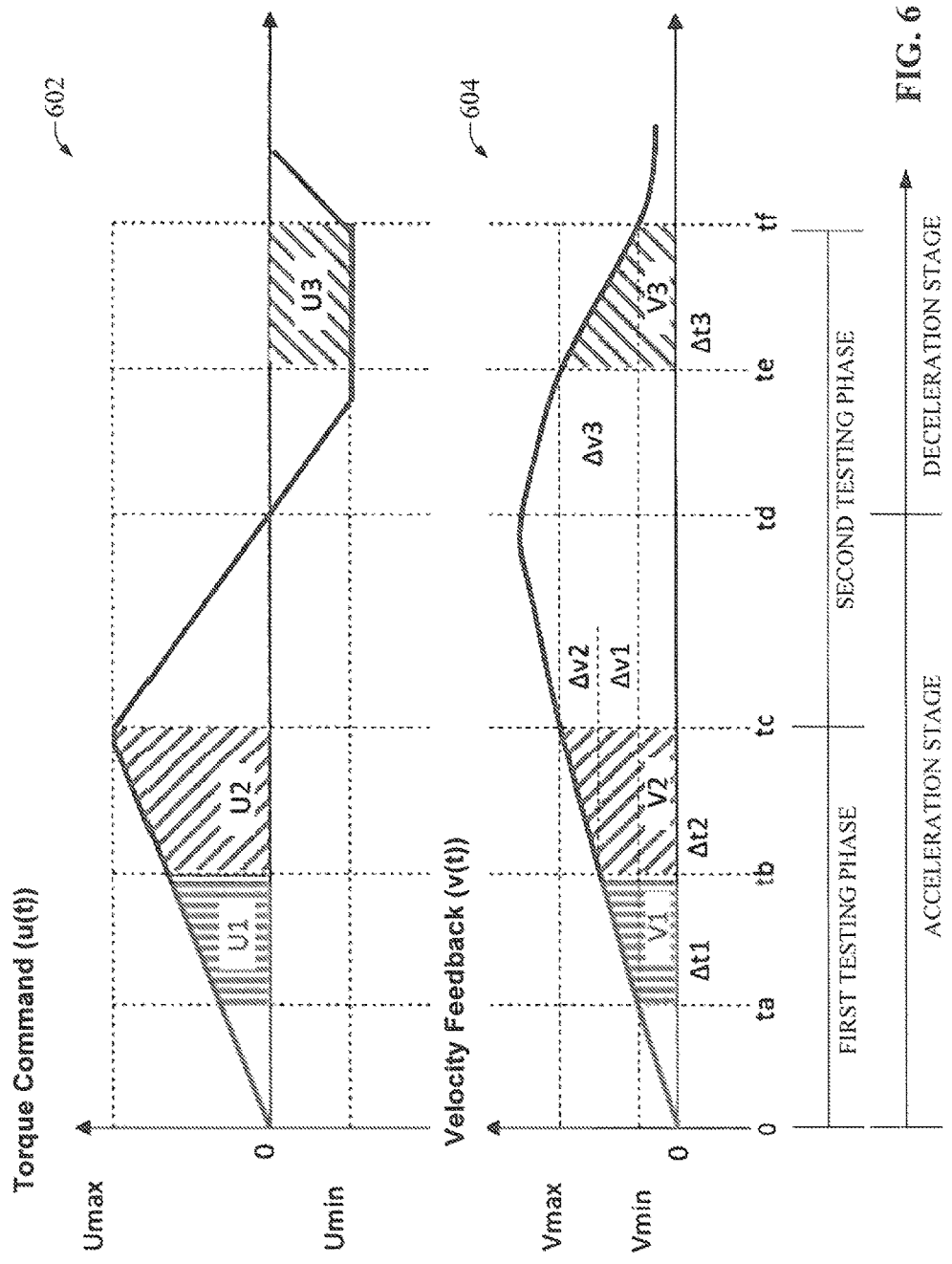
FIG. 6 is a graph of an example torque command signal u(t) and a graph of a corresponding velocity feedback v(t) plotted over time.

In the example illustrated in FIG. 6, when testing begins at time t=0, the applied torque signal u(t) and the motor velocity v(t) are both initially zero when the testing begins at time t=0. However, in some scenarios the testing sequence may begin at a time when the speed of the motion system is non-zero. That is, the motion system does not necessarily need to be at rest when the testing sequence begins.

When the testing sequence begins at time t=0, the torque command generator 304 applies a positive ramp torque, causing the motion system to accelerate. As shown in FIG. 6, the torque command signal u(t) is increased continuously at a substantially constant rate beginning at time t=0. In one or more embodiments, the rate at which torque command signal is increased (that is, the slope of u(t)) can be configured as a user-defined parameter of the estimation system 302 (e.g., via interface component 312). During this first phase of the testing sequence, the torque command signal u(t) continues to increase until either the velocity of the motion system v(t) reaches Vmax, or the torque command signal u(t) reaches Umax. In the illustrated example, the torque command signal reaches Umax just prior to the velocity of the motion system reaching Vmax. Accordingly, the torque command generator 304 holds the torque command signal at Umax while the velocity of the motion system continues to increase in response to the applied torque command signal. When the velocity v(t) reaches Vmax at time t=tc, the estimation system begins the second phase of the testing sequence. In some embodiments, if velocity v(t) does not reach Vmax within a defined timeout period after torque command signal has reached Umax (e.g., if Vmax was inadvertently set higher than the physical velocity limit of the motion system), the estimation system 302 can initiate a suitable timeout handling routine. This timeout handling routine may involve, for example, aborting the testing sequence and displaying an error message via interface component 312.

When the velocity v(t) reaches Vmax at time t=tc, the torque command generator 304 begins the second phase of the testing sequence by ramping the torque command signal u(t) downward toward Umin, causing the motion system to decelerate. Similar to the first phase of the test, the rate at which the torque command signal u(t) is decreased can be set by the user in one or more embodiments. As the torque command u(t) is decreased, the motor will continue to accelerate for a brief time (between time t=tc to td), though at a decreasing rate of acceleration, until the value of the torque command u(t) becomes less than the friction force of the motion system, at which time the motor will begin to decelerate (at time t=td). Since the motor was still accelerating when the velocity v(t) reached Vmax at time t=tc, the velocity will continue past Vmax for some time after the torque command begins decreasing, as shown in FIG. 6.

For this second phase of the test sequence, the torque command generator 304 will continue ramping down the torque command signal u(t) until either the torque command signal reaches Umin, or the velocity of the motion system v(t) decelerates to Vmin. In the illustrated example, the torque command signal u(t) decreases to Umin before the velocity v(t) reaches Vmin. Accordingly, the torque command generator 304 holds the torque command signal at Umin u(t) while the velocity continues to decelerate toward Vmin. As in the first phase of the testing sequence, the estimator system may be configured to initiate an error handling routine if the velocity v(t) does not decelerate to Vmin within a define time period after the torque command signal begins decreasing. Since Umin is set to be less than zero in this example sequence, the torque command signal u(t) decreases to zero at time t=td and continues decreasing as a negative torque value of increasing magnitude until Umin is reached. This negative torque value causes the motion system to decelerate at a faster rate relative to the acceleration of the first phase.

When the velocity of the motion system v(t) reaches Vmin at time t=tf, the torque command generator 304 begins ramping the torque command signal back to zero, allowing the motion system to coast to a resting state as indicated by the tapering end of the v(t) curve in FIG. 6. At this point, the estimation system 302 has the data required to calculate estimates for the inertia and friction coefficients for the mechanical system.

The testing sequence described above in connection with FIG. 6 is only intended to represent an example, non-limiting testing sequence. It is to be understood that any suitable testing sequence that continuously varies the torque command u(t) over time and measures a corresponding velocity profile v(t) for the motion system is within the scope of certain embodiments of this disclosure. For example, although the foregoing example describes the torque command u(t) as changing direction in response to the velocity v(t) reaching the respective velocity checkpoints, some test sequences may include phases in which the torque command u(t) only changes its rate of increase or decrease when the velocity checkpoint is reached, without altering the direction of the torque command (e.g., an increasing torque command may continue to increase in response to v(t) reaching a phase checkpoint, but at a slower rate).

As the foregoing testing sequence is performed, the inertia and friction estimation system 402 records both the torque command signal u(t) generated by torque command generator 304 and the corresponding motor velocity v(t) read by the velocity monitoring component 306. These torque and velocity curves characterize the motion system 524 such that accurate estimates of the inertia, Coulomb friction coefficient, and viscous friction coefficient can be determined based on the curves. In one or more embodiments, after the testing sequence described above has been executed and the data representing u(t) and v(t) has been obtained, the coefficient estimation component 308 calculates estimates of J, $B_v$, and $B_c$ based on integrals of u(t) and v(t) over specific time ranges of the testing sequence. The following illustrates an example technique for leveraging integrals of u(t) and v(t) to derive estimates for the inertia and friction coefficients for a motion system.

A motion system can be described by the differential equation:

$$J\dot{v}(t) = -B_v v(t) - B_c \text{sign}(v(t)) + u(t) \quad (1)$$

where J is the inertia, $B_c$ is the Coulomb friction coefficient, $B_v$ is the viscous friction coefficient, u(t) is the torque command signal, v(t) is the corresponding velocity of the motion system in response to the torque signal u(t) (e.g., u(t) and v(t) described above in connection with FIGS. 5 and 6), and $$\text{sign}(x) = \begin{cases} 1, & x > 0 \\ 0, & x = 0 \\ -1, & x < 0 \end{cases} \quad (2)$$

Referring to the torque and velocity graphs 602 and 604 in FIG. 6, the time period during which the torque command signal is positive (from time t=0 to td) is designated as an acceleration stage, and the time period during which the torque command signal is negative (from time t=td until the motion system decelerates to a resting state) is designated as a deceleration stage.

For the purposes of determining estimates of the inertia and friction coefficients, the coefficient estimation component 308 designates multiple periods within the acceleration and deceleration stages with respect to the predefined velocity checkpoints Vmin and Vmax. In particular, since the system will be solving for three variables (J, $B_v$, and $B_c$), the coefficient estimation component 308 designates at least three periods within the acceleration and deceleration stages in order to solve for J, $B_v$, and $B_c$ based on equation (1) above. In the present example, only three periods are designated. However, in some embodiments the coefficient estimation component 308 can be configured to designate more than three periods.

To determine the first and second periods, the coefficient estimation component 308 first determines the portion of the acceleration stage during which the velocity is between Vmin and Vmax. This portion of the acceleration stage is represented in FIG. 6 as the period between time t=ta and tc. The coefficient estimation component 308 then divides this portion of the acceleration stage into two periods. In the example curves in FIG. 6, the first period derived in this manner is the duration between time t=ta and tb, and the second period is the duration between time t=tb and tc. Any suitable criteria can be used to select a transition time tb between the first and second periods, provided time t=tb is a point in time between times t=ta and tc. For example, some embodiments of the estimation system may be configured to define time t=tb as the midway point between time t=ta (the time at which the velocity of the motion system reached Vmin) and time t=tc (the time at which the velocity reached Vmax). In another example embodiment, the estimation system may be configured to determine the time at which the velocity of the motion system reaches the middle point between Vmax and Vmin during the acceleration stage, and designate this time to be time t=tb. Other techniques for selecting time t=tb are also within the scope of one or more embodiments of this disclosure.

The third period is defined as the portion of the deceleration stage during which the velocity of the motion system is between Vmax and Vmin. In the example curves of FIG. 6, this third period is represented as the period between time t=te and ff. This period is not divided, but instead is maintained as a single period.

After the test data has been collected and the three periods described above have been identified, the coefficient estimation component 308 generates estimates of J, $B_v$, and $B_c$ according to the following procedure. First, the coefficient estimation component 308 integrates both sides of equation (1) above for each of the three designated time periods. For the first time period (time t=ta to tb), integrating both sides of equation (1) yields:

$$J(v(t_b)-v(t_a))=-B_v\int_{t_a}^{t_b}v(t)dt-B_c(t_b-t_a)+\int_{t_a}^{t_b}u(t)dt \quad (3)$$

For the second time period (time t=tb to tc), integrating both sides of equation (1) yields:

$$J(v(t_c)-v(t_b))=-B_v\int_{t_b}^{t_c}v(t)dt-B_c(t_c-t_b)+\int_{t_b}^{t_c}u(t)dt \quad (4)$$

For the third time period (time t=te to tf), integrating both sides of equation (1) yields:

$$J(v(t_f)-v(t_e))=-B_v\int_{t_e}^{t_f}v(t)dt-B_c(t_f-t_e)+\int_{t_e}^{t_f}u(t)dt \quad (5)$$

Equations (3), (4), and (5) can be represented in simplified form by making the following substitutions:

$$\Delta v_1 = v(t_b)-v(t_a) \quad (6)$$

$$\Delta v_2 = v(t_c)-v(t_b) \quad (7)$$

$$\Delta v_3 = v(t_f)-v(t_e) \quad (8)$$

$$V_1 = \int_{t_a}^{t_b}v(t)dt \quad (9)$$

$$V_2 = \int_{t_b}^{t_c}v(t)dt \quad (10)$$

$$V_3 = \int_{t_e}^{t_f}v(t)dt \quad (11)$$

$$\Delta t_1 = t_b - t_a \quad (12)$$

$$\Delta t_2 = t_c - t_b \quad (13)$$

$$\Delta t_3 = t_f - t_e \quad (14)$$

$$U_1 = \int_{t_a}^{t_b}u(t)dt \quad (15)$$

$$U_2 = \int_{t_b}^{t_c}u(t)dt \quad (16)$$

$$U_3 = \int_{t_e}^{t_f}u(t)dt \quad (17)$$

In FIG. 6, the integrals $V_1$, $V_2$, and $V_3$ given by equations (9)-(11) above represent the corresponding shaded regions under the velocity curve v(t) for each of the three periods defined above. Likewise, the integrals $U_1$, $U_2$, and $U_3$ given by equations (15)-(17) above represent the corresponding shaded regions under the torque curve u(t) for the three periods. The coefficient estimation component 308 determines estimates for the inertia J, Coulomb friction coefficient $B_c$, and viscous friction coefficient $B_v$ as a function of these integrals, as described below.

The values $\Delta v_1$, $\Delta v_2$, and $\Delta v_3$ given by equations (6), (7), and (8) represent the change in velocity of the motion system between the beginning and end of each of the three periods, respectively. The values $\Delta t_1$, $\Delta t_2$, and $\Delta t_3$ given by equations (12), (13), and (14), represent the durations of each of the three periods.

Substituting the terms given by equations (6)-(17) into equations (3)-(5) yields the following:

$$\Delta v_1 J + V_1 B_v + \Delta t_1 B_c = U_1 \quad (18)$$

$$\Delta v_2 J + V_2 B_v + \Delta t_2 B_c = U_2 \quad (19)$$

$$\Delta v_3 J + V_3 B_v + \Delta t_3 B_c = U_3 \quad (20)$$

Since equations (18)-(20) are linear algebraic equations with full rank, any method can be used to solve for J, $B_v$, and $B_c$. Accordingly, the coefficient estimation component 308 can be configured to solve equations (18)-(20) for a given set of test data representing u(t) and v(t) using any suitable method. For example, in one or more embodiments the coefficient estimation component 308 can be configured to solve equations (18)-(20) using a matrix solution. In such embodiments, equations (18)-(20) can be arranged in matrix form:

$$Ax = b \quad (21)$$

where $$A = \begin{bmatrix} \Delta v_1 & V_1 & \Delta t_1 \\ \Delta v_2 & V_2 & \Delta t_2 \\ \Delta v_3 & V_3 & \Delta t_3 \end{bmatrix} \quad (22)$$

$$b = \begin{bmatrix} U_1 \\ U_2 \\ U_3 \end{bmatrix} \quad (23)$$

$$x = \begin{bmatrix} J \\ B_v \\ B_c \end{bmatrix} \quad (24)$$

Coefficient estimation component 308 can solve equations (22)-(24) for J, $B_v$, and $B_c$ using the solution $$x = A^{-1}b \quad (25)$$

where $A^{-1}$ is the inverse matrix of A, thereby obtaining estimates for J, $B_v$, and $B_c$.

As noted above, although the example embodiments described above designate three time periods over which to integrate u(t) and v(t) in order to yield three equations (3), (4), and (5) (represented in alternate form as equations (18), (19), and (20)), some embodiments of the estimation system can designate more than three periods, yielding a corresponding number of equations which can be solved for J, $B_v$, and $B_c$. If coefficient estimation component 308 is configured to obtain more than three equations based on designation of more than three time periods, such embodiments of the coefficient estimation component 308 can apply a least square error method to solve for J, $B_v$, and $B_c$ as an alternative to the matrix solution described above.

Equations (21)-(25) are example formulas for calculating estimated inertia and friction coefficients for a motion system based on continuous torque and velocity data. However, it is to be appreciated that any suitable formula for calculating these parameters through integration of a continuous torque signal and a corresponding velocity curve are within the scope of certain embodiments of this disclosure.

Moreover, although the examples described above perform integration on the torque command signal u(t) issued by the motion controller to estimate values for J, $B_v$, and $B_c$, some embodiments of estimation system 302 may be configured to use an actual torque measurement for the integration instead of or in addition to the issued torque command signal. In a variation of such an embodiment, the estimation system can be configured to determine the deviation of the actual (measured or estimated) torque of the motion system from the issued torque command signal, and take this deviation into consideration when estimating J, $B_v$, and $B_c$.

Figure 7:
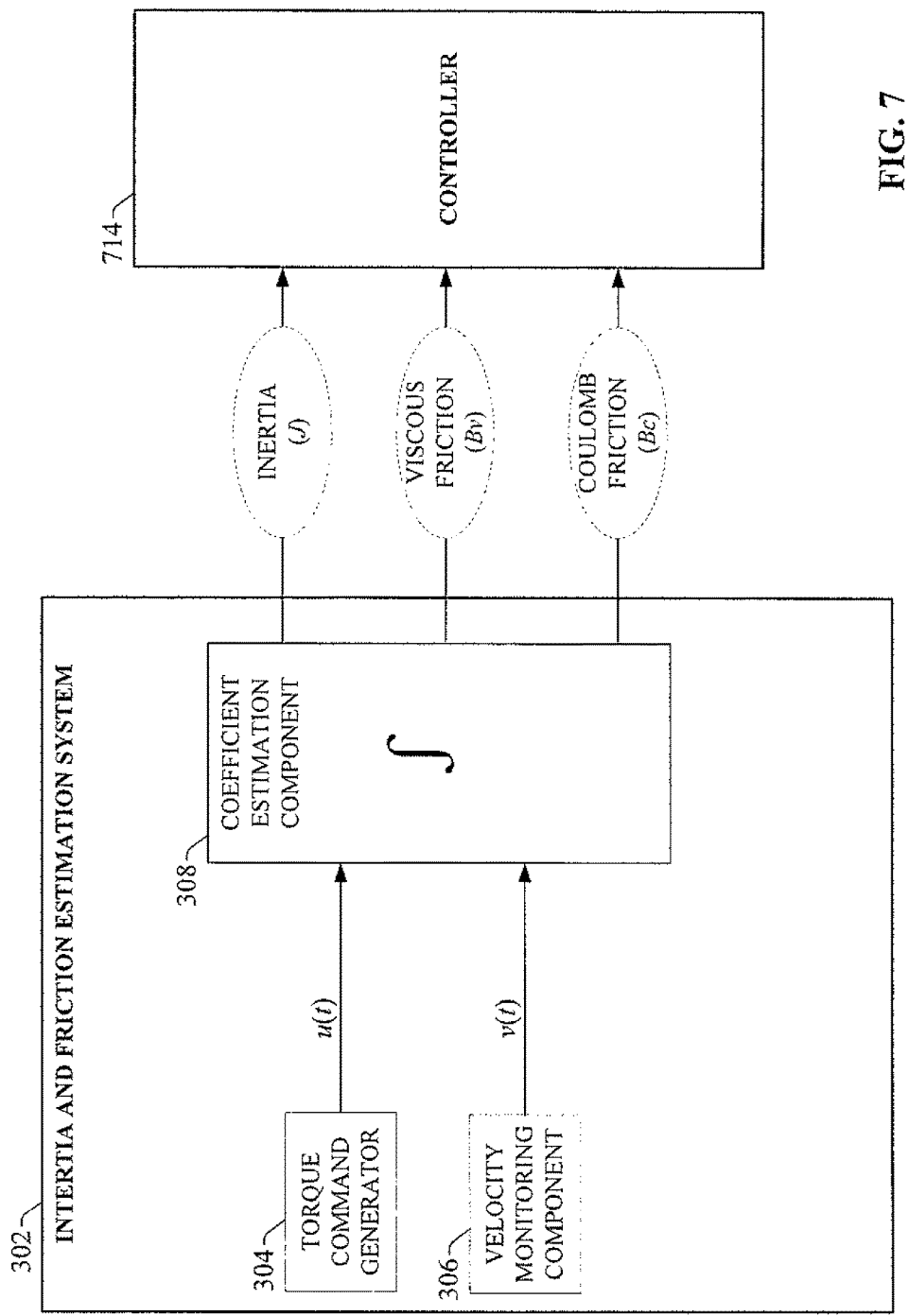
FIG. 7 is a block diagram depicting an inertia and friction estimation system that provides inertia and friction coefficient estimates to a motion controller.

FIG. 7 is a block diagram depicting generation of inertia and friction coefficients by inertia and friction estimation system 302 according to one or more embodiments of the present disclosure. In general, the inertia and friction estimation system 302 generates estimates of the inertia J, viscous friction coefficient $B_v$, and Coulomb friction coefficient $B_c$ for a motion system according to the following procedure. First, the estimation system 302 executes the testing sequence described above in connection with FIGS. 5 and 6 in order to obtain data representing toque and velocity curves u(t) and v(t). Torque command generator 304 and velocity monitoring component provide the data for u(t) and v(t) to the coefficient estimation component 308. Next, the coefficient estimation component 308 can select the three (or more) time periods corresponding to the portions of the torque and velocity curves that will be used as the basis for analysis. For example, the coefficient estimation component 308 can identify the acceleration and deceleration stages of the velocity curve, identify the portion of the acceleration stage during which the velocity is between Vmin and Vmax, and divide this time segment into two time segments to yield the first two periods. The third period can be identified as the portion of the deceleration stage during which the velocity is between Vmax and Vmin. The coefficient estimation component 308 then analyzes the torque and velocity data to determine the integrals, velocity differences, and time durations represented by equations (6)-(17) based on the three selected time periods, and generates equations (18), (19), and (20) using these values. The coefficient estimation component 308 then solves these equations for J, $B_c$, and $B_v$ (e.g., using a matrix solution or other technique) in order to yield estimates of the inertia and friction coefficients, which are then output by the estimation system 302.

In various embodiments, inertia and friction estimation system 302 can output the estimated inertia and friction coefficients in accordance with the requirements of a particular application in which the system operates. For example, as illustrated in FIG. 7, estimation system 302 may provide the estimates of J, $B_v$, and $B_c$ to a motion controller 714, which can use the inertia and friction coefficient estimates to facilitate tuning one or more gain coefficients. In addition or alternatively, estimation system 302 may output the estimated values of J, $B_v$, and $B_c$ to a display device (e.g., via interface component 312) so that the values can be viewed and entered manually into a separate motion control or tuning application. Accurate estimates of the motion system's inertia and friction coefficients can simplify the tuning process and facilitate accurate parameter tuning, resulting in precise and energy-efficient machine motion. Moreover, since the estimation system estimates the inertia and friction coefficients based on data collected over the motion system's entire torque profile (rather than extrapolating based on the system's response to one or more constant torque commands), the inertia and friction coefficient estimates derived by the estimation system 302 are more likely to be accurate over the full operational range of the motion system.

Figure 8:
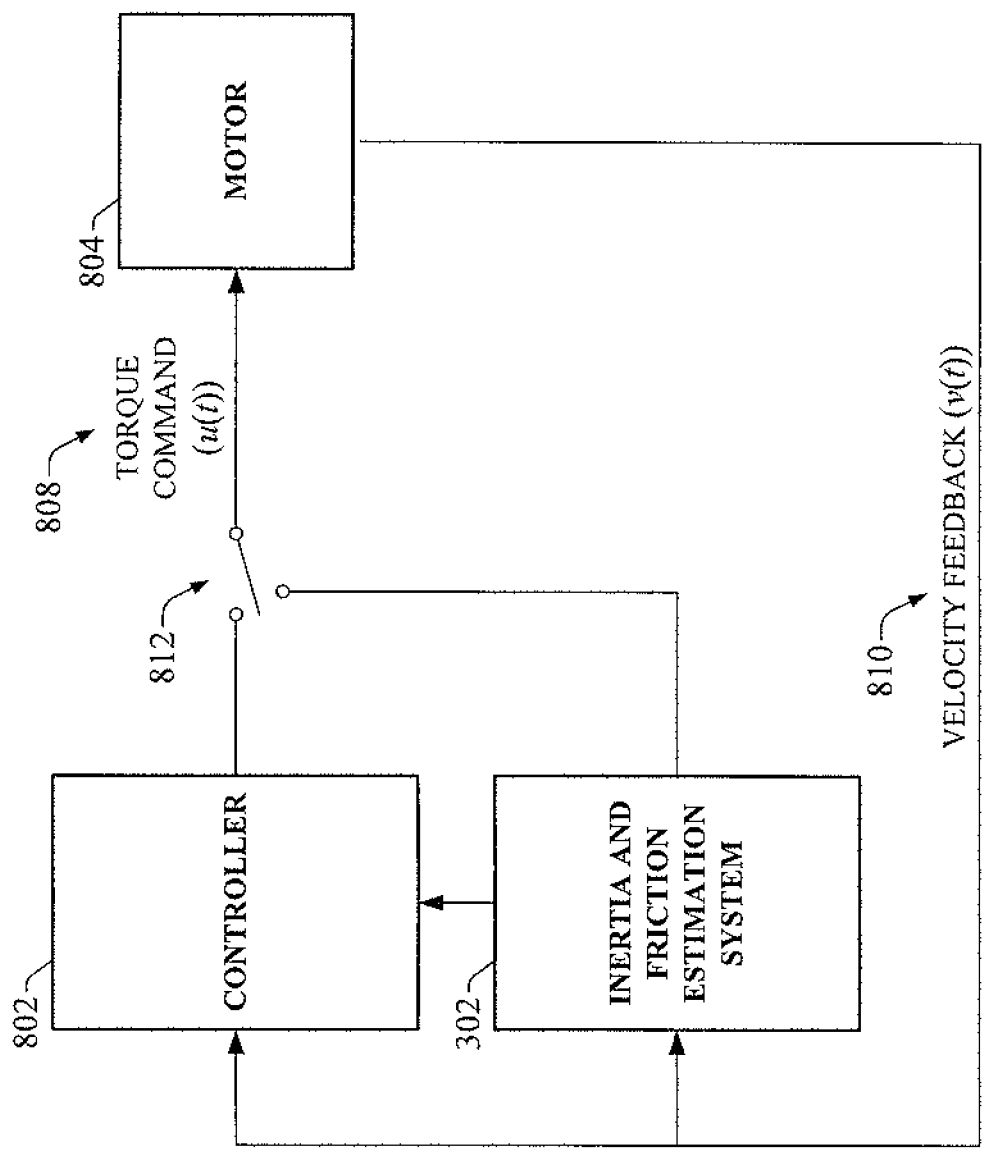
FIG. 8 is a diagram of an architecture in which an inertia and friction estimation system operates as an independent component that is separate from a motion controller.

While the preceding examples have described the estimation system 302 as outputting the torque command u(t) and receiving the velocity feedback v(t) via the motion controller (e.g., controller 518 of FIG. 5), either as a separate component operating through the controller or as an integrated component of the controller, other configurations are within the scope of certain embodiments of this disclosure. For example, FIG. 8 illustrates an architecture in which inertia and friction estimation system 302 operates as an independent component that is separate from motion controller 802. In this example architecture, estimation system 302 is capable of generating its own torque command signal independently of controller 802. A motor 804 being tested and controlled can receive its torque command signal 808 from either controller 802 or estimation system 302 depending on the state of switch 812. The velocity feedback 810 from the motor 804 can be provided to both the controller 802 and estimation system 302. During the testing sequence, switch 812 can be set to convey the torque command signal u(t) generated by the estimation system 302 rather than controller 802. Testing can proceed as described in previous examples, such that estimation system 302 generates estimated values for the inertia J and friction coefficients $B_c$ and $B_v$ for the motion system. Estimation system 302 can then provide the estimated values for J, $B_c$, and $B_v$ to the controller 802, which can use these values to determine suitable controller gain coefficients or other control parameters. Once the controller parameters have been set, switch 812 can be transitioned to connect the motor 804 to the torque command signal 808 generated by controller 802 rather than estimation system 302, and normal operation of the motion system can be carried out using the controller gain coefficients derived based on J, $B_c$, and $B_v$.

Figure 9:
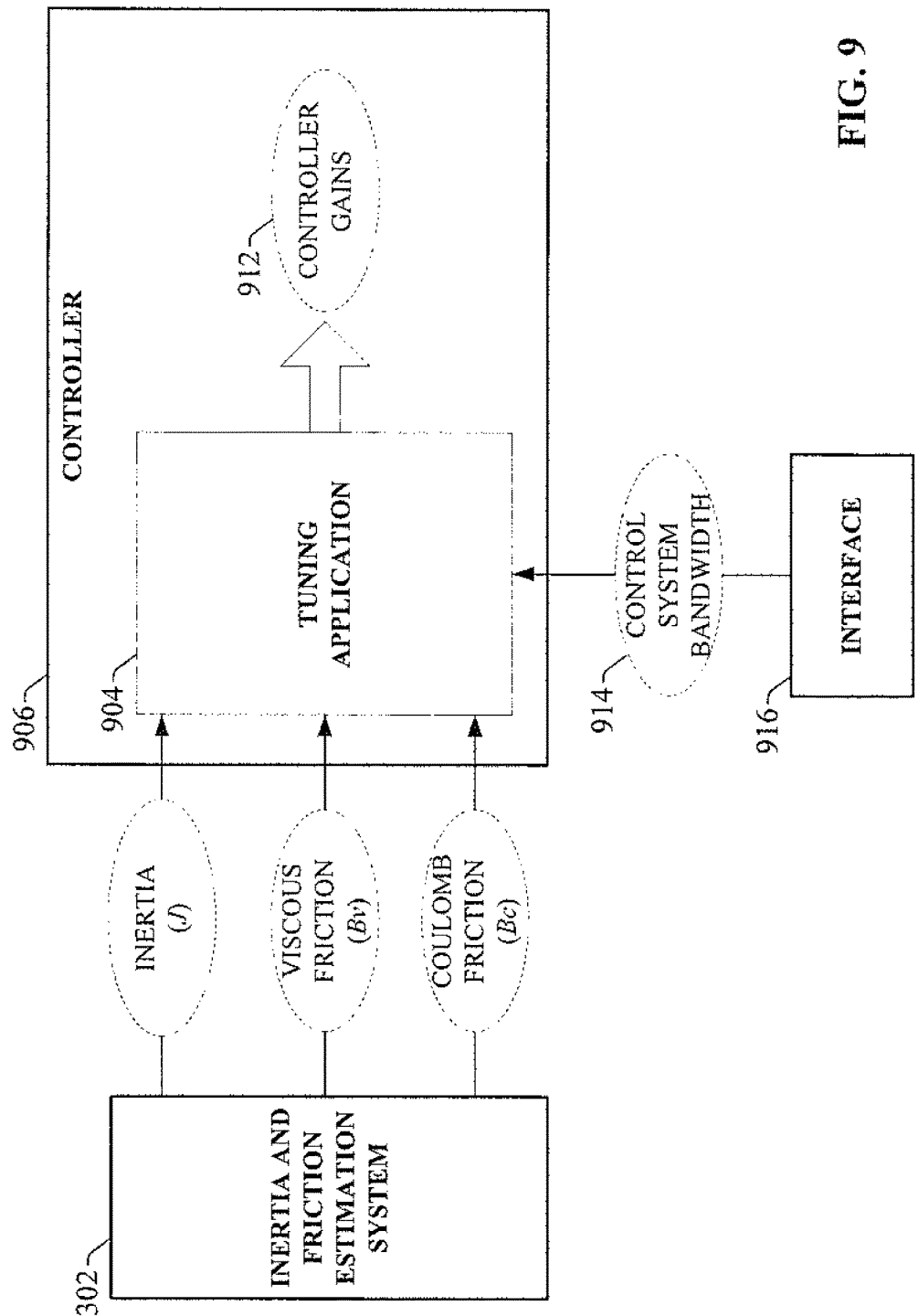
FIG. 9 is a diagram illustrating an example motion control tuning application that utilizes the estimated inertia and friction coefficients generated by an inertia and friction estimation system.

FIG. 9 illustrates an example motion control tuning application that utilizes the estimated inertia and friction coefficients generated by the estimation system 302. In this example, a tuning application 904 is used to tune the controller gains for controller 906, where the controller 906 controls operation of a motor-driven motion system (not shown). Estimation system 302 can generate estimates of the motion system's inertia J, viscous friction coefficient $B_v$, and Coulomb friction coefficient $B_c$ using the techniques described above. Specifically, estimation system 302 instructs controller 906 to send a continuous torque command to the motion system's motor, where the torque command varies continuously over time according to a predefined testing sequence. Alternatively, for embodiments in which estimation system 302 operates independently of controller 906 (as in the example configuration depicted in FIG. 8), the estimation system 302 can generate and send its own continuous torque command to the motion system. The testing sequence can include acceleration and deceleration stages, during which the estimation system 302 monitors and records the velocity of the motion system in response to the applied torque command. At the conclusion of the testing sequence, estimation system 302 can calculate estimates of J, $B_c$, and $B_v$ based at least in part on selected integrals of the time-varying torque command signal and the corresponding time-varying motion system velocity (e.g., based on equations (18), (19), and (20)).

Estimation system 302 can then provide the estimated inertia and friction coefficient values to the tuning application 904. Alternatively, estimation system 302 can render the values of J, $B_c$, and $B_v$ on a user interface, allowing a user to manually enter the estimated inertia and friction coefficients into the tuning application 904. Knowledge of J, $B_c$, and $B_v$ can allow the tuning application 904 to generate suitable estimates for one or more controller gains 912 based on the mechanical properties of the motion system represented by the estimated inertia and friction coefficients. Tuning application 904 can generate suitable values for controller gains 912 as a function of the inertia J, viscous friction coefficient $B_v$, and Coulomb friction coefficient $B_c$, as well as control system bandwidth (e.g., crossover frequency) 914, which can be manually adjusted by the user via interface 916 to achieve desired motion characteristics.

In typical applications, the inertia and friction estimation system described herein can be used to generate reliable estimates of a motion system's inertia J, viscous friction coefficient $B_v$, and Coulomb friction coefficient $B_c$ during initial deployment of a motion control system, prior to normal operation. Specifically, the estimation system can be used in connection with configuring and tuning the controller parameters (e.g., controller gain coefficients) prior to runtime. Once set, these parameters typically remain fixed after system startup, unless it is decided to re-tune the system at a later time. However, in some embodiments, the estimation system can be configured to automatically recalculate values for J, $B_c$, and $B_v$ periodically or continuously during normal closed-loop operation of the motion system. In such embodiments, the estimation system can monitor the torque command output signals issued by the controller in accordance with the user-defined control routines that execute during normal runtime operation (as opposed to the testing sequence described above), as well as the velocity of the motion system during acceleration and deceleration in response to these torque command signals. Using this run-time data, the estimation system can perform the integrations described above—either periodically, continuously, or semi-continuously—to generate updated estimates of J, $B_c$, and $B_v$. Using such configurations, controller gains that are based on estimates of J, $B_c$, and $B_v$ can be dynamically adjusted during normal operation, substantially in real-time, to compensate for gradual changes to the motion system's mechanical properties (e.g., as a result of mechanical wear and tear, changes to the load seen by a motor, addition or erosion of lubricants used in the motion system, etc.).

In the examples illustrated in FIGS. 5, 7, and 9, inertia and friction estimation system 302 is depicted as a separate element from the motion controller. For such configurations, any of components 304, 306, or 308 can exchange data with the controller or other elements of the motion system via any suitable communications means, including but not limited to wired or wireless networking, hardwired data links, or other such communication means. In other embodiments, one or more of components 304, 306, or 308 can be integrated components of a motion controller (e.g., an industrial controller such as a programmable logic controller, a system-on-chip or other type of microcontroller, etc.) For example, one or more of components 304, 306, or 308 can be functional components of the controller's operating system and/or control software executed by one or more processors residing on the controller. Components 304, 306, or 308 can also be hardware components residing within the controller, such as a circuit board or integrated circuit, that exchanges data with other functional elements of the controller. In some embodiments, inertia and friction estimation system 302 may also be an integrated sub-system of a motor drive (e.g., a variable frequency drive or other motor drive). Other suitable implementations are also within the scope of certain embodiments of this disclosure.

Inertia and friction estimation system 302 can be used in connection with substantially any type of motion control application, including but not limited to conveyor control systems, industrial robots, washing machines, centrifuges, pumps, material handling systems, automotive systems, or other such motion control applications.

Figure 10:
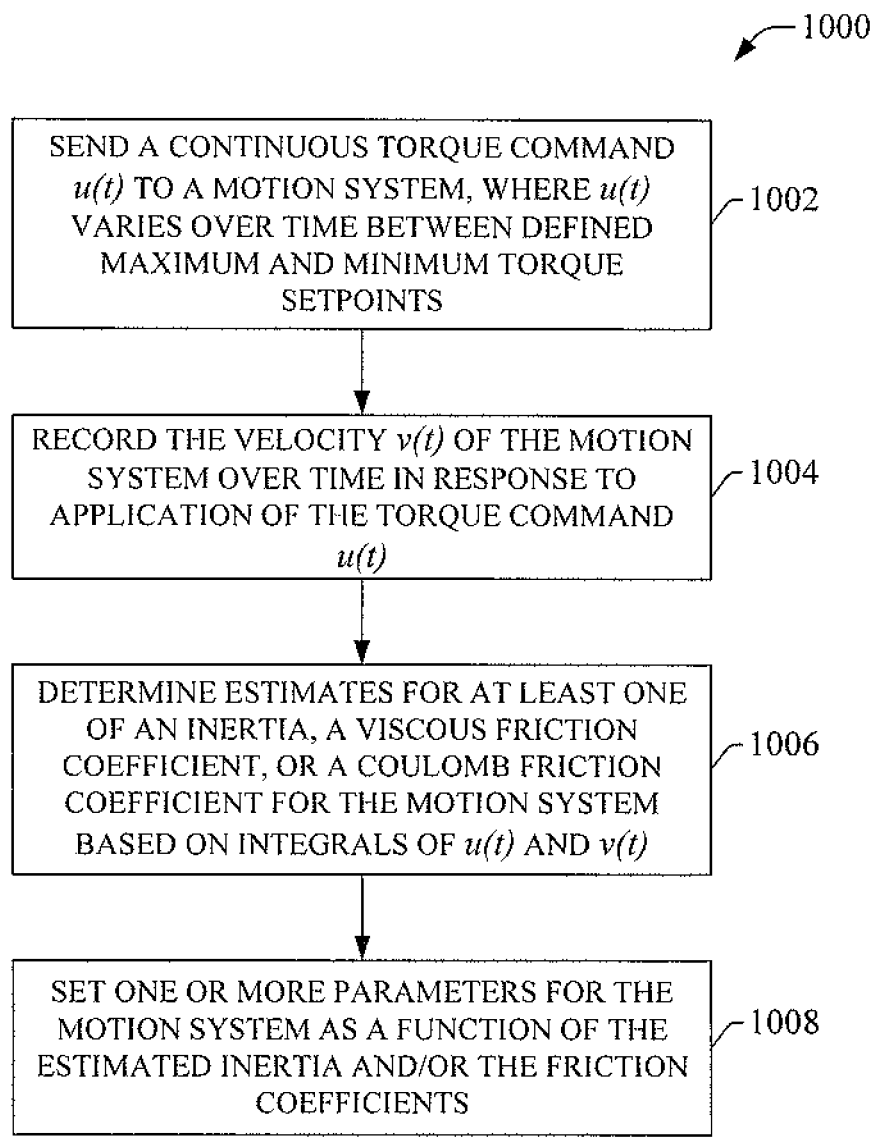
FIG. 10 is a flowchart of an example methodology for estimating an inertia, a Coulomb friction coefficient, and a viscous friction coefficient for a controlled mechanical system.

FIGS. 10-11 illustrate various methodologies in accordance with certain disclosed aspects. While, for purposes of simplicity of explanation, the methodologies are shown and described as a series of acts, it is to be understood and appreciated that the disclosed aspects are not limited by the order of acts, as some acts may occur in different orders and/or concurrently with other acts from that shown and described herein. For example, those skilled in the art will understand and appreciate that a methodology can alternatively be represented as a series of interrelated states or events, such as in a state diagram. Moreover, not all illustrated acts may be required to implement a methodology in accordance with certain disclosed aspects. Additionally, it is to be further appreciated that the methodologies disclosed hereinafter and throughout this disclosure are capable of being stored on an article of manufacture to facilitate transporting and transferring such methodologies to computers.

FIG. 10 illustrates an example methodology 1000 for estimating an inertia, a Coulomb friction coefficient, and a viscous friction coefficient for a controlled mechanical system. Initially, at 1002, a continuous torque command signal u(t) is sent to a controller of a motion system, where torque command signal u(t) varies over time between defined maximum and minimum torque setpoints. In one or more embodiments, the torque command signal u(t) can accord to a predefined testing sequence, such that the output of u(t) depends on the phase of the testing sequence and the response of the mechanical system relative to one or more user-defined setpoints. The test sequence can comprise both acceleration and deceleration stages, corresponding to increasing and decreasing motor speeds, respectively.

At 1004, the velocity v(t) of the motion system in response to the torque command signal u(t) is recorded. Thus, upon completion of the testing sequence, data curves for both the applied torque command signal u(t) and the resultant motion system velocity v(t) are obtained for the duration of the test sequence.

At 1006, estimates for at least one of the inertia, the viscous friction coefficient, or the Coulomb friction coefficient of the motion system are calculated based on integrals of the torque curve u(t) and the velocity curve v(t). In one or more embodiments, three time periods within the duration of the test sequence can be selected, and equations defining a relationship between the inertia, Coulomb friction coefficient, and viscous friction coefficient can be obtained based on integrals of the torque and velocity curves over the three time segments (e.g., using equations (18), (19), and (20) above, or other suitable equations). The three equations can then be solved for the inertia, Coulomb friction coefficient, and viscous friction coefficient to obtain estimates of those three parameters. At 1008, one or more parameters for the motion system are set as a function of the estimated inertia and/or friction coefficients calculated at step 1006. In a non-limiting example, one or more controller gain coefficients can be set based on the estimated inertia and/or friction coefficients calculated according to steps 1002-1006.

Figure 11A:
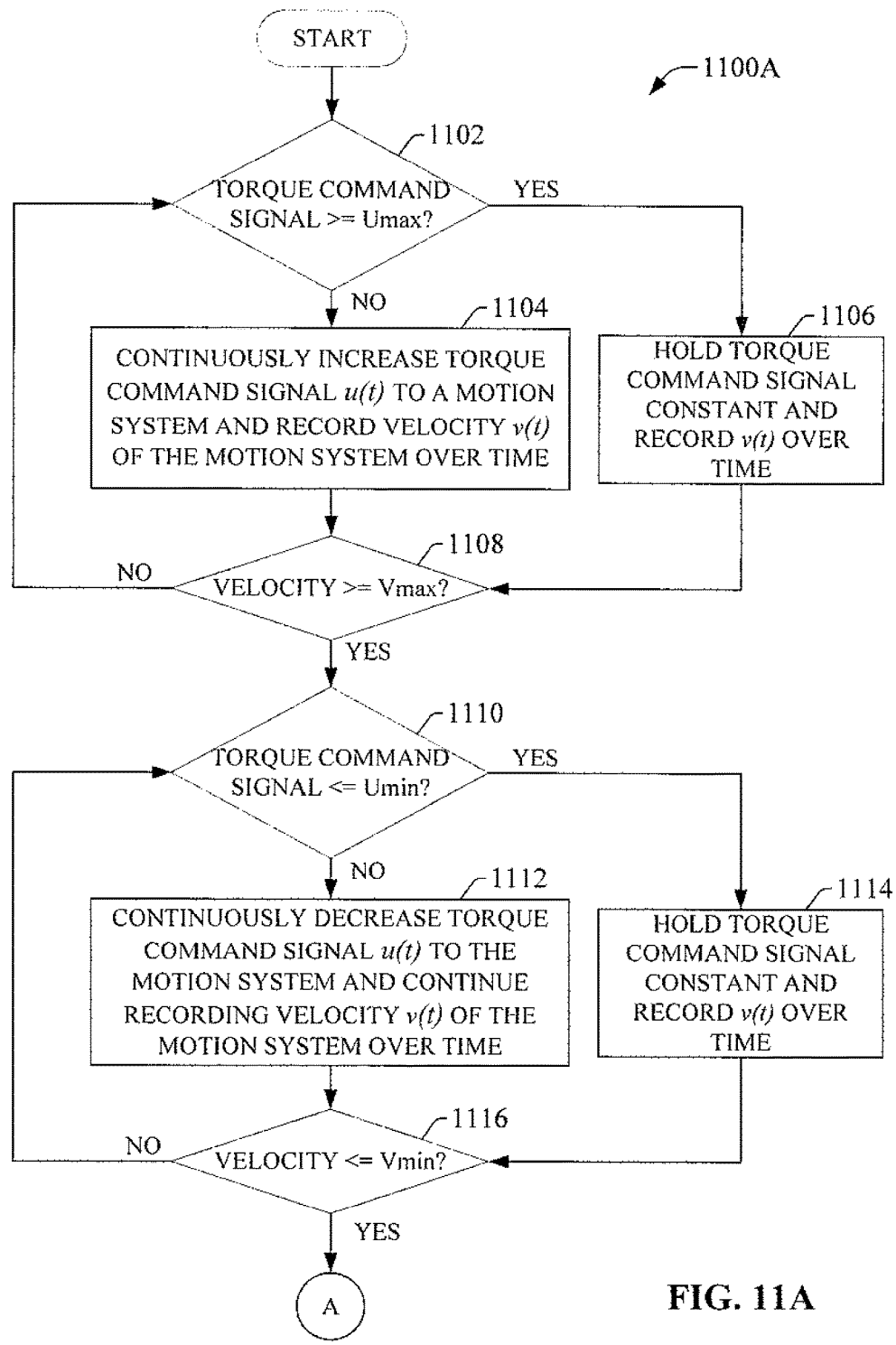
FIGS. 11A and 11B are flowcharts of an example methodology for executing a testing sequence on a motion system in order to estimate the inertia, viscous friction, and Coulomb friction of the system.

FIG. 11A illustrates a first part of an example methodology 1100A for executing a testing sequence on a motion system in order to estimate the inertia, viscous friction coefficient, and Coulomb friction coefficient of the system. Initially, at 1102, a determination is made regarding whether a torque command signal sent to a motion system (e.g., a torque command signal sent to a controller that controls the speed and/or position of a motion system) is greater than or equal to an upper torque limit Umax. In one or more embodiments, this upper torque limit can be a user-defined limit provided via a user interface. If the torque command signal is not greater than or equal to Umax, the methodology proceeds to step 1104, where the torque command signal u(t) is continuously increased, and the velocity v(t) of the motion system in response to the applied torque command signal is recorded.

At 1108, a determination is made regarding whether the velocity of the motion system is greater than or equal to a velocity checkpoint value Vmax. In one or more embodiments, this checkpoint value may be set by a user via a user interface. If the velocity is not greater than or equal to Vmax, the methodology returns to step 1102, where it is again determined whether the torque command signal is greater than or equal to Umax. Steps 1102, 1104, and 1108 are repeated continuously until either the torque command signal reaches Umax at step 1102, or the velocity of the motion system reaches Vmax at step 1108. If the torque command signal reaches Umax at step 1102 before the velocity reaches Vmax, the methodology moves to step 1106, where the torque command signal is held constant while the motion system continues to accelerate. In one or more embodiments, if the velocity does not reach Vmax at step 1108 within a defined time period, an appropriate error handling routine may be executed (e.g., the methodology may halt the testing sequence and output an error message to an interface display).

When the velocity of the motion system reaches Vmax at step 1108, the methodology proceeds to step 1110, where a determination is made regarding whether the torque command signal is less than or equal to a lower torque limit Umin. As with Umax, this lower torque limit may be set by a user via a user interface. In some scenarios, the lower torque limit Umin may be less than zero. If the torque command signal is not less than or equal to Umin at step 1110, the methodology moves to step 1112, where the torque command signal to the motion system is continuously decreased, and the velocity of the motion system in response to the torque command signal continues to be recorded.

As the torque command signal continues decreasing, a determination is made at step 1116 regarding whether the velocity of the motion system has decreased to a value less than or equal to another velocity checkpoint value Vmin, which is set to be less than checkpoint value Vmax. If the velocity is not less than or equal to Vmin, the methodology returns to step 1110, where a determination is again made regarding whether the torque command signal is less than or equal to Umin. Steps 1110, 1112, and 1116 are repeated continuously until either the torque command signal becomes less than or equal to Umin at step 1110, or the velocity of the motion system becomes less than or equal to Vmin at step 1116.

If the torque command signal becomes less than or equal to Umin at step 1110 before the velocity of the motion system becomes less than or equal to Vmin, the methodology moves to step 1114, where the torque command signal is held constant while the motion system continues to decelerate. The torque command signal continues to be held constant until the velocity becomes less than or equal to Vmin at step 1116.

Figure 11B:
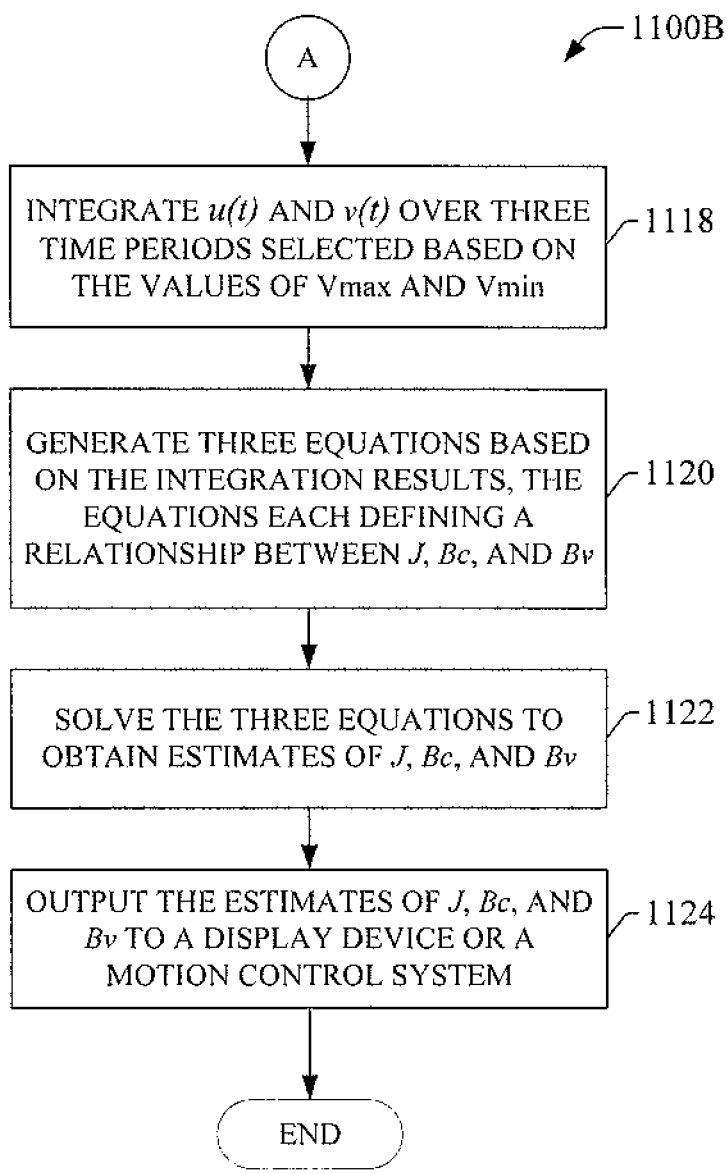

The second part of the example methodology 1100B continues in FIG. 11B. At the end of the test sequence described by methodology 1100A, the system has a record of data describing the time-varying torque command signal u(t) sent to the motion system during the testing sequence, as well as measured velocity v(t) of the motion system over time in response to the applied torque command signal. At 1118, the torque and velocity curves u(t) and v(t) are integrated over three time periods selected based on the values of the velocity checkpoints Vmax and Vmin. For example, in one or more embodiments, the time segment beginning at the time when the velocity of the motion system first reaches Vmin during acceleration and ending at a time before the velocity first reaches Vmax can be designated as the first time period, and the time segment beginning at the end of the first time period and ending at a time when the velocity first reaches Vmax during acceleration can be designated as the second time period. The third time period can be designated as the time segment beginning when the velocity of the decelerating motion system returns to Vmax and ending when the velocity returns to Vmin. These designated time periods are only intended to be exemplary, and it is to be appreciated that other criteria for selected three time segments over which to integrate the torque and velocity curves are within the scope of one or more embodiments of this disclosure. Six integral results are derived at step 1118—three integral results $U_1$, $U_2$, and $U_3$ derived by integrating the torque curve over the respective three time periods, and three integral results $V_1$, $V_2$, and $V_3$ derived by integrating the velocity curve over the respective three time periods.

At 1120, three equations are generated based on the integral results obtained at step 1118, where each of the three equations define a relationship between inertia J, Coulomb friction coefficient $B_c$, and viscous friction coefficient $B_v$. For example, the equations can be derived by substituting the integrals $U_1$, $U_2$, $U_3$, $V_1$, $V_2$, and $V_3$ into equations (18), (19), and (20) described above.

At 1122, the three equations generated at step 1120 are solved to obtain estimates of J, $B_c$, and $B_v$. For example, the three equations can be solved using a matrix solution, based on equations (21)-(25) above. However, other suitable techniques can be used to solve for the three variables without departing from the scope of one or more embodiments of this disclosure. At 1124, the estimates of J, $B_c$, and $B_v$ derived at step 1122 are output, either to a display device, to the motion control system, or to another external system that uses the estimated inertia and friction coefficients in connection with designing or tuning the motion system.

Exemplary Networked and Distributed Environments

One of ordinary skill in the art can appreciate that the various embodiments described herein can be implemented in connection with any computer or other client or server device, which can be deployed as part of a computer network or in a distributed computing environment, and can be connected to any kind of data store where media may be found. In this regard, the various embodiments of the video editing system described herein can be implemented in any computer system or environment having any number of memory or storage units (e.g., memory 316 of FIG. 3), and any number of applications and processes occurring across any number of storage units. This includes, but is not limited to, an environment with server computers and client computers deployed in a network environment or a distributed computing environment, having remote or local storage. For example, with reference to FIG. 3, the torque command generator 304, velocity monitoring component 306, coefficient estimation component 308, and interface component 312 can be stored on a single memory 316 associated with a single device, or can be distributed among multiple memories associated with respective multiple devices. Similarly, torque command generator 304, velocity monitoring component 306, coefficient estimation component 308, and interface component 312 can be executed by a single processor 314, or by multiple distributed processors associated with multiple devices.

Distributed computing provides sharing of computer resources and services by communicative exchange among computing devices and systems. These resources and services include the exchange of information, cache storage and disk storage for objects. These resources and services can also include the sharing of processing power across multiple processing units for load balancing, expansion of resources, specialization of processing, and the like. Distributed computing takes advantage of network connectivity, allowing clients to leverage their collective power to benefit the entire enterprise. In this regard, a variety of devices may have applications, objects or resources that may participate in the various embodiments of this disclosure.

Figure 12:
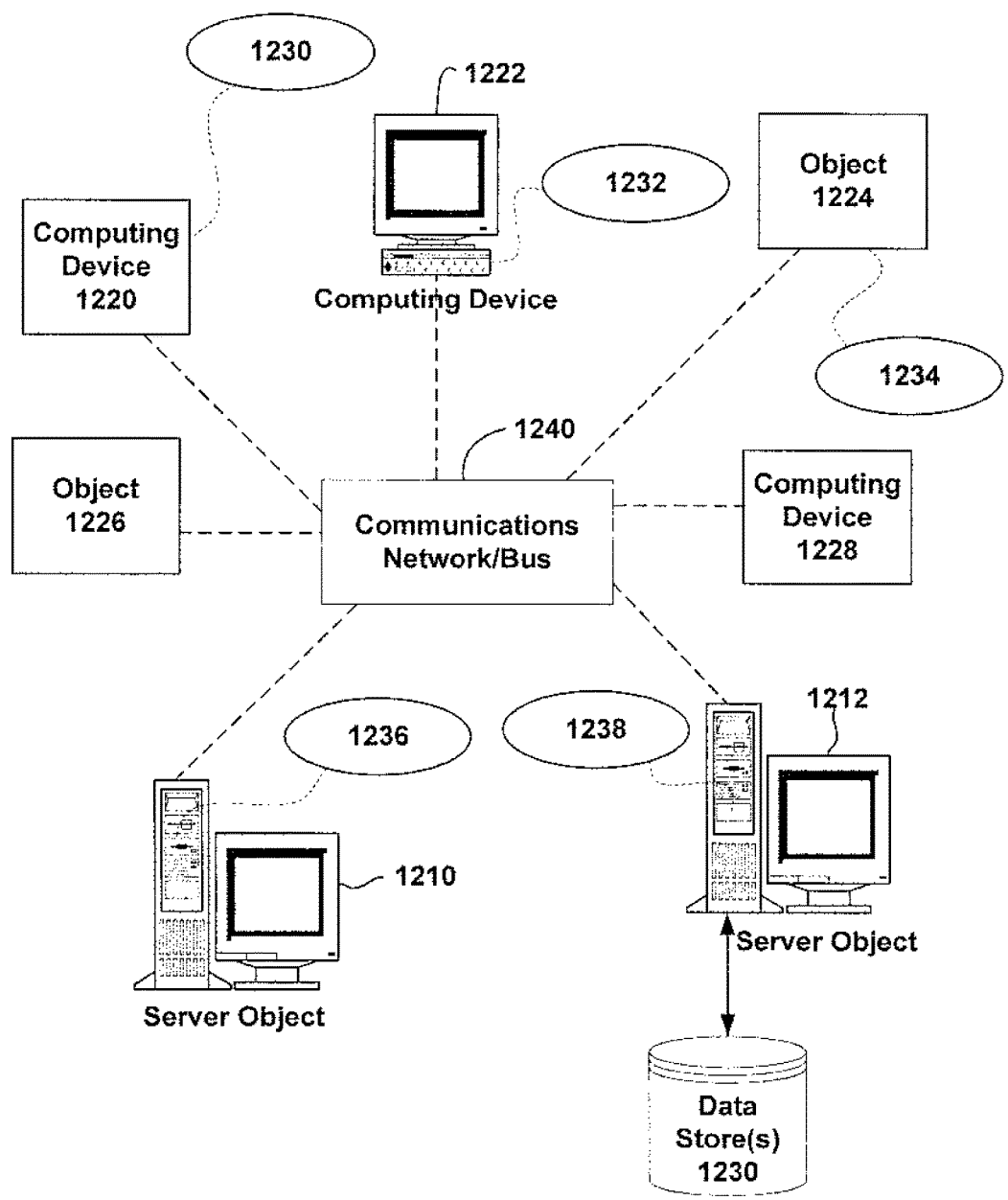
FIG. 12 is a block diagram representing an exemplary networked or distributed computing environment for implementing one or more embodiments described herein.

FIG. 12 provides a schematic diagram of an exemplary networked or distributed computing environment. The distributed computing environment includes computing objects 1210, 1212, etc. and computing objects or devices 1220, 1222, 1224, 1226, 1228, etc., which may include programs, methods, data stores, programmable logic, etc., as represented by applications 1230, 1232, 1234, 1236, 1238. It can be appreciated that computing objects 1210, 1212, etc. and computing objects or devices 1220, 1222, 1224, 1226, 1228, etc. may comprise different devices, such as personal digital assistants (PDAs), audio/video devices, mobile phones, MP3 players, personal computers, laptops, tablets, etc., where embodiments of the inertia estimator described herein may reside on or interact with such devices.

Each computing object 1210, 1212, etc. and computing objects or devices 1220, 1222, 1224, 1226, 1228, etc. can communicate with one or more other computing objects 1210, 1212, etc. and computing objects or devices 1220, 1222, 1224, 1226, 1228, etc. by way of the communications network 1240, either directly or indirectly. Even though illustrated as a single element in FIG. 12, communications network 1240 may comprise other computing objects and computing devices that provide services to the system of FIG. 12, and/or may represent multiple interconnected networks, which are not shown. Each computing object 1210, 1212, etc. or computing objects or devices 1220, 1222, 1224, 1226, 1228, etc. can also contain an application, such as applications 1230, 1232, 1234, 1236, 1238 (e.g., inertia and friction estimation system 302 or components thereof), that might make use of an API, or other object, software, firmware and/or hardware, suitable for communication with or implementation of various embodiments of this disclosure.

There are a variety of systems, components, and network configurations that support distributed computing environments. For example, computing systems can be connected together by wired or wireless systems, by local networks or widely distributed networks. Currently, many networks are coupled to the Internet, which provides an infrastructure for widely distributed computing and encompasses many different networks, though any suitable network infrastructure can be used for exemplary communications made incident to the systems as described in various embodiments herein.

Thus, a host of network topologies and network infrastructures, such as client/server, peer-to-peer, or hybrid architectures, can be utilized. The "client" is a member of a class or group that uses the services of another class or group. A client can be a computer process, e.g., roughly a set of instructions or tasks, that requests a service provided by another program or process. A client process may utilize the requested service without having to "know" all working details about the other program or the service itself.

In a client/server architecture, particularly a networked system, a client can be a computer that accesses shared network resources provided by another computer, e.g., a server. In the illustration of FIG. 12, as a non-limiting example, computing objects or devices 1220, 1222, 1224, 1226, 1228, etc. can be thought of as clients and computing objects 1210, 1212, etc. can be thought of as servers where computing objects 1210, 1212, etc. provide data services, such as receiving data from client computing objects or devices 1220, 1222, 1224, 1226, 1228, etc., storing of data, processing of data, transmitting data to client computing objects or devices 1220, 1222, 1224, 1226, 1228, etc., although any computer can be considered a client, a server, or both, depending on the circumstances. Any of these computing devices may be processing data, or requesting transaction services or tasks that may implicate the techniques for systems as described herein for one or more embodiments.

A server is typically a remote computer system accessible over a remote or local network, such as the Internet or wireless network infrastructures. The client process may be active in a first computer system, and the server process may be active in a second computer system, communicating with one another over a communications medium, thus providing distributed functionality and allowing multiple clients to take advantage of the information-gathering capabilities of the server. Any software objects utilized pursuant to the techniques described herein can be provided standalone, or distributed across multiple computing devices or objects.

In a network environment in which the communications network/bus 1240 is the Internet, for example, the computing objects 1210, 1212, etc. can be Web servers, file servers, media servers, etc. with which the client computing objects or devices 1220, 1222, 1224, 1226, 1228, etc. communicate via any of a number of known protocols, such as the hypertext transfer protocol (HTTP). Computing objects 1210, 1212, etc. may also serve as client computing objects or devices 1220, 1222, 1224, 1226, 1228, etc., as may be characteristic of a distributed computing environment.

Exemplary Computing Device

Figure 13:
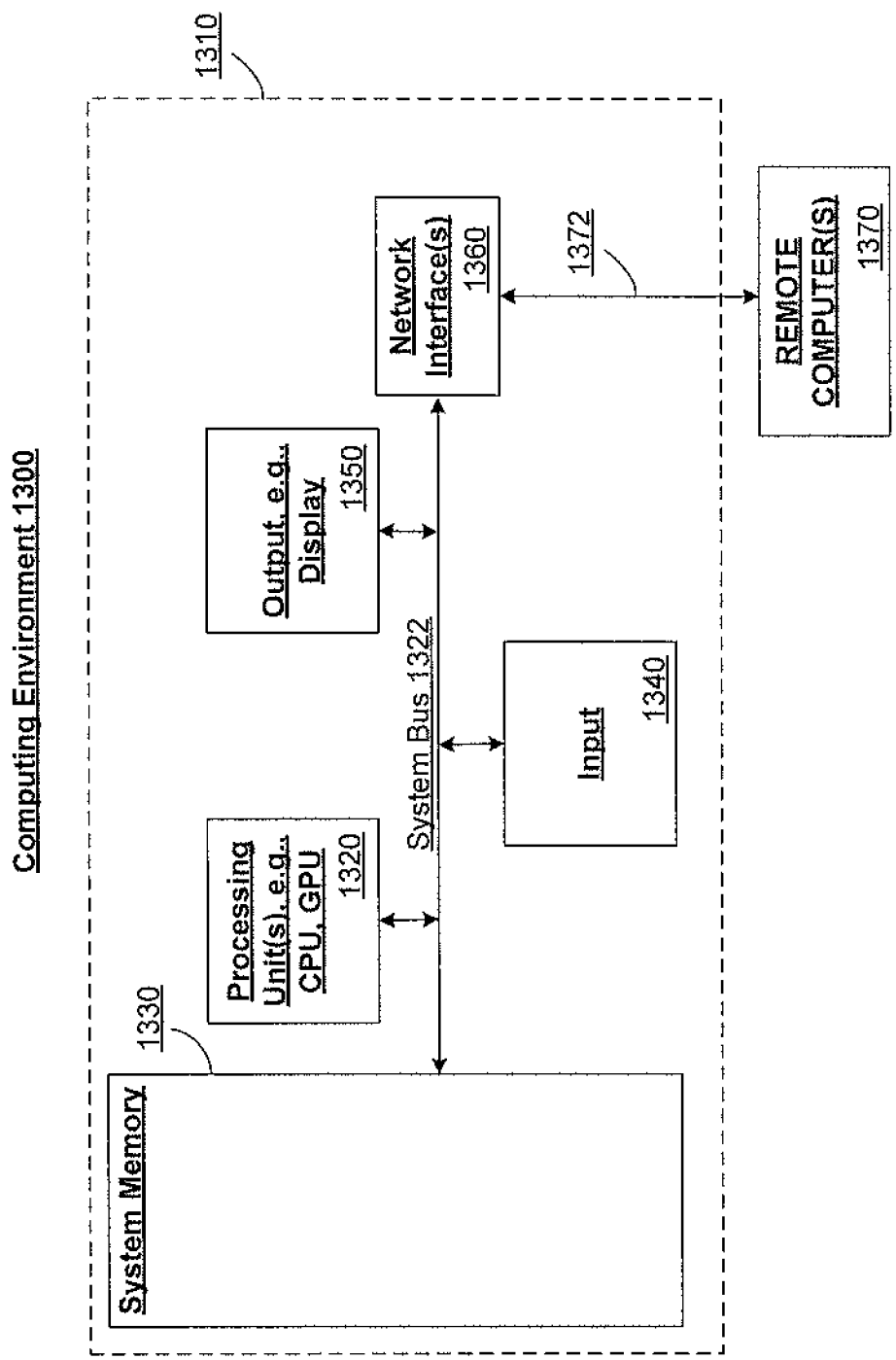
FIG. 13 is a block diagram representing an exemplary computing system or operating environment for implementing one or more embodiments described herein.

As mentioned, advantageously, the techniques described herein can be applied to any suitable device. It is to be understood, therefore, that handheld, portable and other computing devices and computing objects of all kinds are contemplated for use in connection with the various embodiments. Accordingly, the below computer described below in FIG. 13 is but one example of a computing device. Additionally, a suitable server can include one or more aspects of the below computer, such as a media server or other media management server components.

Although not required, embodiments can partly be implemented via an operating system, for use by a developer of services for a device or object, and/or included within application software that operates to perform one or more functional aspects of the various embodiments described herein. Software may be described in the general context of computer executable instructions, such as program modules, being executed by one or more computers, such as client workstations, servers or other devices. Those skilled in the art will appreciate that computer systems have a variety of configurations and protocols that can be used to communicate data, and thus, no particular configuration or protocol is to be considered limiting.

FIG. 13 thus illustrates an example of a suitable computing system environment 1300 in which one or aspects of the embodiments described herein can be implemented, although as made clear above, the computing system environment 1300 is only one example of a suitable computing environment and is not intended to suggest any limitation as to scope of use or functionality. Neither is the computing system environment 1300 be interpreted as having any dependency or requirement relating to any one or combination of components illustrated in the exemplary computing system environment 1300.

With reference to FIG. 13, an exemplary computing device for implementing one or more embodiments in the form of a computer 1310 is depicted. Components of computer 1310 may include, but are not limited to, a processing unit 1320, a system memory 1330, and a system bus 1322 that couples various system components including the system memory to the processing unit 1320. Processing unit 1320 may, for example, perform functions associated with processor(s) 314 of estimation system 302, while system memory 1330 may perform functions associated with memory 316.

Computer 1310 typically includes a variety of computer readable media and can be any available media that can be accessed by computer 1310. The system memory 1330 may include computer storage media in the form of volatile and/or nonvolatile memory such as read only memory (ROM) and/or random access memory (RAM). By way of example, and not limitation, system memory 1330 may also include an operating system, application programs, other program modules, and program data.

A user can enter commands and information into the computer 1310 through input devices 1340, non-limiting examples of which can include a keyboard, keypad, a pointing device, a mouse, stylus, touchpad, touchscreen, trackball, motion detector, camera, microphone, joystick, game pad, scanner, or any other device that allows the user to interact with computer 1310. A monitor or other type of display device is also connected to the system bus 1322 via an interface, such as output interface 1350. In addition to a monitor, computers can also include other peripheral output devices such as speakers and a printer, which may be connected through output interface 1350. In one or more embodiments, input devices 1340 can provide user input to interface component 312, while output interface 1350 can receive information relating to operations of the inertia and friction estimation system 302 from interface component 312.

The computer 1310 may operate in a networked or distributed environment using logical connections to one or more other remote computers, such as remote computer 1370. The remote computer 1370 may be a personal computer, a server, a router, a network PC, a peer device or other common network node, or any other remote media consumption or transmission device, and may include any or all of the elements described above relative to the computer 1310. The logical connections depicted in FIG. 13 include a network 1372, such local area network (LAN) or a wide area network (WAN), but may also include other networks/buses e.g., cellular networks.

As mentioned above, while exemplary embodiments have been described in connection with various computing devices and network architectures, the underlying concepts may be applied to any network system and any computing device or system in which it is desirable to publish or consume media in a flexible way.

Also, there are multiple ways to implement the same or similar functionality, e.g., an appropriate API, tool kit, driver code, operating system, control, standalone or downloadable software object, etc. which enables applications and services to take advantage of the techniques described herein. Thus, embodiments herein are contemplated from the standpoint of an API (or other software object), as well as from a software or hardware object that implements one or more aspects described herein. Thus, various embodiments described herein can have aspects that are wholly in hardware, partly in hardware and partly in software, as well as in software.

The word "exemplary" is used herein to mean serving as an example, instance, or illustration. For the avoidance of doubt, the aspects disclosed herein are not limited by such examples. In addition, any aspect or design described herein as "exemplary" is not necessarily to be construed as preferred or advantageous over other aspects or designs, nor is it meant to preclude equivalent exemplary structures and techniques known to those of ordinary skill in the art. Furthermore, to the extent that the terms "includes," "has," "contains," and other similar words are used in either the detailed description or the claims, for the avoidance of doubt, such terms are intended to be inclusive in a manner similar to the term "comprising" as an open transition word without precluding any additional or other elements.

Computing devices typically include a variety of media, which can include computer-readable storage media (e.g., memory 316) and/or communications media, in which these two terms are used herein differently from one another as follows. Computer-readable storage media can be any available storage media that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

On the other hand, communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

As mentioned, the various techniques described herein may be implemented in connection with hardware or software or, where appropriate, with a combination of both. As used herein, the terms "component," "system" and the like are likewise intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on computer and the computer can be a component. One or more components may reside within a process and/or thread of execution and a component may be localized on one computer and/or distributed between two or more computers. Further, a "device" can come in the form of specially designed hardware; generalized hardware made specialized by the execution of software thereon that enables the hardware to perform specific function (e.g., coding and/or decoding); software stored on a computer readable medium; or a combination thereof.

The aforementioned systems have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it is to be noted that one or more components may be combined into a single component providing aggregate functionality or divided into several separate sub-components, and that any one or more middle layers, such as a management layer, may be provided to communicatively couple to such sub-components in order to provide integrated functionality. Any components described herein may also interact with one or more other components not specifically described herein but generally known by those of skill in the art.

In order to provide for or aid in the numerous inferences described herein (e.g. inferring audio segments), components described herein can examine the entirety or a subset of the data to which it is granted access and can provide for reasoning about or infer states of the system, environment, etc. from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data.

Such inference can result in the construction of new events or actions from a set of observed events and/or stored event data, whether or not the events are correlated in close temporal proximity, and whether the events and data come from one or several event and data sources. Various classification (explicitly and/or implicitly trained) schemes and/or systems (e.g., support vector machines, neural networks, expert systems, Bayesian belief networks, fuzzy logic, data fusion engines, etc.) can be employed in connection with performing automatic and/or inferred action in connection with the claimed subject matter.

A classifier can map an input attribute vector, x=(x1, x2, x3, x4, xn), to a confidence that the input belongs to a class, as by f(x)=confidence(class). Such classification can employ a probabilistic and/or statistical-based analysis (e.g., factoring into the analysis utilities and costs) to prognose or infer an action that a user desires to be automatically performed. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

In view of the exemplary systems described above, methodologies that may be implemented in accordance with the described subject matter will be better appreciated with reference to the flowcharts of the various figures (e.g., FIGS. 10 and 11). While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Where non-sequential, or branched, flow is illustrated via flowchart, it can be appreciated that various other branches, flow paths, and orders of the blocks, may be implemented which achieve the same or a similar result. Moreover, not all illustrated blocks may be required to implement the methodologies described hereinafter.

In addition to the various embodiments described herein, it is to be understood that other similar embodiments can be used or modifications and additions can be made to the described embodiment(s) for performing the same or equivalent function of the corresponding embodiment(s) without deviating there from. Still further, multiple processing chips or multiple devices can share the performance of one or more functions described herein, and similarly, storage can be effected across a plurality of devices. Accordingly, the invention is not to be limited to any single embodiment, but rather can be construed in breadth, spirit and scope in accordance with the appended claims.

What is claimed is:

1. A method for estimating parameters of a motion system, comprising:
  generating, by a system comprising at least one processor, a torque command signal that varies continuously over time;
  measuring, by the system, velocity data for a motion device representing a velocity of the motion system in response to the torque command signal;
  determining, by the system, estimated values of an inertia, a viscous friction coefficient, and a Coulomb friction coefficient of the motion system based at least in part on integrals of the velocity data over three time ranges and integrals of the torque command signal over the three time ranges; and
  outputting, by the system, the estimated values to a tuning application that tunes controller gains of an industrial controller based on the estimated values of the inertia, the viscous friction coefficient, and the Coulomb friction coefficient.

2. The method of claim 1, wherein the generating the torque command signal comprises adjusting the torque command signal in accordance with a predefined testing sequence.

3. The method of claim 2, wherein the adjusting the torque command signal comprises changing at least one of a direction or a rate of change of the torque command signal in response to the velocity of the motion system reaching a predefined velocity checkpoint.

4. The method of claim 1, wherein the determining comprises:

integrating the torque command signal and the velocity data over a first time range of the three time ranges to yield $U_1$ and $V_1$, respectively, wherein the first time range begins at time t=ta and ends at time t=tb;

integrating the torque command signal and the velocity data over a second time range of the three time ranges to yield $U_2$ and $V_2$, respectively, wherein the second time range begins at time t=tb and ends at time t=tc;

integrating the torque command signal and the velocity data over a third time range of the three time ranges to yield $U_3$ and $V_3$, respectively, wherein the third time range begins at time t=te and ends at time t=tf;

determining the estimated values of the inertia, the viscous friction coefficient, and the Coulomb friction coefficient as a function of $U_1$, $V_1$, $U_2$, $V_2$, $U_3$, and $V_3$, where:

$U_1 = \int_{t_a}^{t_b} u(t)dt$, $V_1 = \int_{t_a}^{t_b} v(t)dt$, $U_2 = \int_{t_b}^{t_c} u(t)dt$, $V_2 = \int_{t_b}^{t_c} v(t)dt$, $U_3 = \int_{t_e}^{t_f} u(t)dt$, $V_3 = \int_{t_e}^{t_f} v(t)dt$ u(t) is the torque command signal as a function of time, and v(t) is the velocity data as a function of time.

5. The method of claim 4, wherein the determining the estimated values of the inertia, the viscous friction coefficient, and the Coulomb friction coefficient comprises solving equations $\Delta v_1 J + V_1 B_v + \Delta t_1 B_c = U_1$, $\Delta v_2 J + V_2 B_v + \Delta t_2 B_c = U_2$, and $\Delta v_3 J + V_3 B_v + \Delta t_3 B_c = U_3$ for J, Bv, and Bc,
where:
J is the inertia,
Bv is the viscous friction coefficient,
$B_C$ is the Coulomb friction coefficient,
$\Delta v_1$ is a change of the velocity of the motion system between time t=ta and time t=tb,
$\Delta v_2$ is a change of the velocity of the motion system between time t=tb and time t=tc,
$\Delta v_3$ is a change of the velocity of the motion system between time t=te and time t=tf,
$\Delta t_1$ is a difference between time t=ta and time t=tb,
$\Delta t_2$ is a difference between time t=tb and time t=tc, and
$\Delta t_3$ is a difference between time t=te and time t=tf.

6. The method of claim 5, wherein the solving comprises the equations using a matrix solution.

7. The method of claim 1, further comprising determining at least one controller gain coefficient for the motion system based on at least one of the inertia, the viscous friction coefficient, or the Coulomb friction coefficient.

8. A system for estimating parameters of a motion system, comprising:
a memory;
a processor configured to execute computer-executable components stored on the memory, the computer-executable components comprising:
a torque command generator configured to generate a torque command signal that varies continuously over time during a testing sequence;
a velocity monitoring component configured to obtain velocity data representing a velocity of a motion system over time in response to the torque command signal;
a coefficient estimation component configured to estimate an inertia, a Coulomb friction coefficient, and a viscous friction coefficient of the motion system based on integrals of the torque command signal over three time ranges and integrals of the velocity data over the three time ranges; and
an interface component configured to send values of at least one of the inertia, the Coulomb friction coefficient, or the viscous friction coefficient to a tuning component that tunes controller gains of an industrial controller as a function of the values of at least one of the inertia, the Coulomb friction coefficient, or the viscous friction coefficient.

9. The system of claim 8, wherein the three time ranges are respective time segments of the testing sequence.

10. The system of claim 8, wherein the torque command generator is further configured to control the torque command signal in accordance with a torque function u(t), where u(t) is based on a set of predefined instructions associated with respective phases of the testing sequence.

11. The system of claim 10, wherein the respective phases are triggered in response to the velocity of the motion system reaching defined velocity checkpoint values.

12. The system of claim 8, wherein the coefficient estimation component is further configured to estimate the inertia, the Coulomb friction coefficient, and the viscous friction coefficient as a function of $U_1$, $V_1$, $U_2$, $V_2$, $U_3$, and $V_3$,
where:

$U_1 = \int_{t_a}^{t_b} u(t)dt$, $V_1 = \int_{t_a}^{t_b} v(t)dt$, $U_2 = \int_{t_b}^{t_c} u(t)dt$, $V_2 = \int_{t_b}^{t_c} v(t)dt$, $U_3 = \int_{t_e}^{t_f} u(t)dt$, $V_3 = \int_{t_e}^{t_f} v(t)dt$, v(t) is the velocity of the motion system as a function of time,
ta is a value of time t at a beginning of a first time range of the three time ranges,
tb is a value of time t at an end of the first time range and a beginning of the second time range of the three time ranges,
tc is a value of time t at an end of the second time range,
te is a value of time t at a beginning of a third time range of the three time ranges, and
tf is a value of time t at an end of the third time range.

13. The system of claim 12, wherein the coefficient estimation component is further configured to estimate the inertia, the Coulomb friction coefficient, and the viscous friction coefficient based on equations:

$\Delta v_1 J + V_1 B_v + \Delta t_1 B_c = U_1$, $\Delta v_2 J + V_2 B_v + \Delta t_2 B_c = U_2$, and $\Delta v_3 J + V_3 B_v + \Delta t_3 B_c = U_3$, where:
J is the inertia,
Bv is the viscous friction coefficient,
$B_C$ is the Coulomb friction coefficient,
$\Delta v_1$ is a change in the velocity of the motion system between time t=ta and time t=tb,
$\Delta v_2$ is a change of the velocity of the motion system between time t=tb and time t=tc,
$\Delta v_3$ is a change of the velocity of the motion system between time t=te and time t=tf,
$\Delta t_1$ is a difference between time t=ta and time t=tb,
$\Delta t_2$ is a difference between time t=tb and time t=tc, and
$\Delta t_3$ is a difference between time t=te and time t=tf.

14. The system of claim 13, wherein the friction coefficient component is configured to solve the equations using a matrix solution.

15. The system of claim 8, wherein the tuning component is configured to generate at least one controller gain coefficient as a function of at least one of the inertia, the Coulomb friction coefficient, or the viscous friction coefficient.

16. A non-transitory computer-readable medium having stored thereon computer-executable instructions that, in response to execution, cause a computer system to perform operations, comprising:
generating a torque command signal that varies continuously over time;
recording velocity data representing a velocity of the motion system in response to the torque command signal;
determining estimated values of an inertia, a viscous friction coefficient, and a Coulomb friction coefficient of the motion system based at least in part on integrals of the velocity data over three time ranges and integrals of the torque command signal over the three time ranges; and
outputting the estimated values to a tuning application that tunes gains of a motion controller based on the estimated values of the inertia, the viscous friction coefficient, and the Coulomb friction coefficient.

17. The non-transitory computer-readable medium of claim 16, wherein the determining comprises:
integrating the torque command signal and the velocity data over a first time range of the three time ranges to yield $U_1$ and $V_1$, respectively, wherein the first time range begins at time t=ta and ends at time t=tb;
integrating the torque command signal and the velocity data over a second time range of the three time ranges to yield $U_2$ and $V_2$, respectively, wherein the second time range begins at time t=tb and ends at time t=tc;
integrating the torque command signal and the velocity data over a third time range of the three time ranges to yield $U_3$ and $V_3$, respectively, wherein the third time range begins at time t=te and ends at time t=tf;
determining the estimated values of the inertia, the viscous friction coefficient, or the Coulomb friction coefficient as a function of $U_1$, $V_1$, $U_2$, $V_2$, $U_3$, and $V_3$,
where:

$U_1 = \int_{t_a}^{t_b} u(t)dt,$ $V_1 = \int_{t_a}^{t_b} v(t)dt,$ $U_2 = \int_{t_b}^{t_c} u(t)dt,$ $V_2 = \int_{t_b}^{t_c} v(t)dt,$ $U_3 = \int_{t_e}^{t_f} u(t)dt,$ $V_3 = \int_{t_e}^{t_f} v(t)dt$ u(t) is the torque command signal as a function of time, and
v(t) is the velocity data as a function of time.

18. The non-transitory computer-readable medium of claim 17, wherein the determining the estimated values of the inertia, the viscous friction coefficient, and the Coulomb friction coefficient comprises solving equations $\Delta v_1 J + V_1 B_v + \Delta t_1 B_c = U_1,$ $\Delta v_2 J + V_2 B_v + \Delta t_2 B_c = U_2,$ and $\Delta v_3 J + V_3 B_v + \Delta t_3 B_c = U_3$ for J, Bv, and Bc,
where:
J is the inertia,
Bv is the viscous friction coefficient,
$B_C$ is the Coulomb friction coefficient,
$\Delta v_1$ is a change of the velocity of the motion system between time t=ta and time t=tb,
$\Delta v_2$ is a change of the velocity of the motion system between time t=tb and time t=tc,
$\Delta v_3$ is a change of the velocity of the motion system between time t=te and time t=tf,
$\Delta t_1$ is a difference between time t=ta and time t=tb,
$\Delta t_2$ is a difference between time t=tb and time t=tc, and
$\Delta t_3$ is a difference between time t=te and time t=tf.

19. The system of claim 8, wherein the motion system is at least one of a conveyor control system, an industrial robot system, a washing machine, a centrifuge, a pump, a material handling system, or an automotive system.

20. The non-transitory computer-readable medium of claim 16, wherein the motion system is at least one of a conveyor control system, an industrial robot system, a washing machine, a centrifuge, a pump, a material handling system, or an automotive system.

* * * * *